US012636253B2

(12) United States Patent
Kirkpatrick

(10) Patent No.: US 12,636,253 B2
(45) Date of Patent: *May 26, 2026

(54) MODIFIED RELEASE COMPOSITIONS OF NAFAMOSTAT AND METHODS OF USING SAME

(71) Applicant: Ensysce Biosciences Inc., La Jolla, CA (US)

(72) Inventor: Lynn Kirkpatrick, La Jolla, CA (US)

(73) Assignee: Ensysce Biosciences Inc., La Jolla, CA (US)

( * ) Notice: Subject to any disclaimer, the term of this patent is extended or adjusted under 35 U.S.C. 154(b) by 737 days.

This patent is subject to a terminal disclaimer.

(21) Appl. No.: 17/689,255

(22) Filed: Mar. 8, 2022

(65) Prior Publication Data

US 2022/0287975 A1 Sep. 15, 2022

Related U.S. Application Data

(60) Provisional application No. 63/158,654, filed on Mar. 9, 2021.

(51) Int. Cl.

| | |
|---|---|
| ***A61K 9/16*** | (2006.01) |
| ***A61K 9/00*** | (2006.01) |
| ***A61K 31/216*** | (2006.01) |

(52) U.S. Cl.

CPC .......... *A61K 9/1676* (2013.01); *A61K 9/1611* (2013.01); *A61K 9/1623* (2013.01); (Continued)

(58) Field of Classification Search

None

See application file for complete search history.

(56) References Cited

U.S. PATENT DOCUMENTS 3,842,064 A 10/1974 Greven
3,850,904 A 11/1974 Greven
(Continued)

FOREIGN PATENT DOCUMENTS

DE 1041052 10/1958
DE 1493824 5/1969
(Continued)

OTHER PUBLICATIONS

English Google translation of Yakida et al. JPH0940579—published Feb. 10, 1997 (Year: 1997).*
(Continued)

*Primary Examiner* — Aradhana Sasan
(74) *Attorney, Agent, or Firm* — Khin K. Chin; Bozicevic, Field & Francis LLP

(57) ABSTRACT

Aspects of the present disclosure include a composition of nafamostat or a pharmaceutically acceptable salt thereof that provides for controlled release of nafamostat or pharmaceutically acceptable salt thereof to a subject for an extended period of time. Compositions according to certain embodiments include a plurality of controlled release beads where each bead includes a core, an active agent layer having nafamostat or a pharmaceutically acceptable salt thereof and a controlled release layer having one or more polymers formulated in an amount sufficient to provide for controlled release of the nafamostat or pharmaceutically 10 acceptable salt thereof. Methods for administering (e.g., orally) the controlled release nafamostat compositions to a subject are also described.

15 Claims, 13 Drawing Sheets

(52) U.S. Cl.
CPC .......... *A61K 9/1647* (2013.01); *A61K 9/1652* (2013.01); *A61K 31/216* (2013.01); *A61K 9/0053* (2013.01)

(56) References Cited

U.S. PATENT DOCUMENTS

| | | | |
|---|---|---|---|
| 3,853,836 A | 12/1974 | Greven | |
| 3,853,838 A | 12/1974 | Greven | |
| 3,875,137 A | 4/1975 | Jones et al. | |
| 4,104,371 A | 8/1978 | Greven et al. | |
| 4,297,346 A | 10/1981 | Rips et al. | |
| 4,454,338 A | 6/1984 | Fujii et al. | |
| 4,532,255 A | 7/1985 | Fujii et al. | |
| 5,109,118 A | 4/1992 | Mizushima et al. | |
| 5,217,987 A | 6/1993 | Berger | |
| 5,352,704 A | 10/1994 | Okuyama et al. | |
| 5,958,459 A | 9/1999 | Chasin et al. | |
| 6,245,802 B1 | 6/2001 | Iyengar et al. | |
| 6,388,122 B1 | 5/2002 | Kido et al. | |
| 6,586,196 B1 | 7/2003 | Bronstein et al. | |
| 7,060,290 B1 | 6/2006 | Morimoto et al. | |
| 7,105,486 B2 | 9/2006 | Mickle et al. | |
| 7,189,414 B2 | 3/2007 | Rubinstein et al. | |
| 7,223,735 B2 | 5/2007 | Mickle et al. | |
| 7,655,630 B2 | 2/2010 | Mickle et al. | |
| 7,893,105 B2 | 2/2011 | Xiang et al. | |
| 8,163,701 B2 | 4/2012 | Jenkins et al. | |
| 8,217,005 B2 | 7/2012 | Jenkins et al. | |
| 8,497,237 B2 | 7/2013 | Jenkins et al. | |
| 8,569,228 B2 | 10/2013 | Jenkins et al. | |
| 8,685,916 B2 | 4/2014 | Jenkins et al. | |
| 8,802,681 B2 | 8/2014 | Jenkins et al. | |
| 8,921,418 B2 | 12/2014 | Jenkins et al. | |
| 8,962,547 B2 | 2/2015 | Jenkins et al. | |
| 9,023,860 B2 | 5/2015 | Jenkins et al. | |
| 9,040,032 B2 | 5/2015 | Jenkins et al. | |
| 9,095,627 B2 | 8/2015 | Jenkins et al. | |
| 9,139,612 B2 | 9/2015 | Jenkins et al. | |
| 2003/0035831 A1 | 2/2003 | Modi | |
| 2003/0180352 A1 | 9/2003 | Patel et al. | |
| 2004/0063628 A1 | 4/2004 | Piccariello et al. | |
| 2005/0054561 A1 | 3/2005 | Mickle et al. | |
| 2005/0080012 A1 | 4/2005 | Mickle et al. | |
| 2005/0176644 A1 | 8/2005 | Mickle et al. | |
| 2005/0176645 A1 | 8/2005 | Mickle et al. | |
| 2005/0228001 A1* | 10/2005 | Hanson .................. | A61K 45/06 514/257 |
| 2007/0042955 A1 | 2/2007 | Mickle et al. | |
| 2007/0082929 A1 | 4/2007 | Gant et al. | |
| 2007/0093420 A1 | 4/2007 | Yeomans et al. | |
| 2007/0123468 A1 | 5/2007 | Jenkins et al. | |
| 2007/0203055 A1 | 8/2007 | Mickle et al. | |
| 2007/0292511 A1* | 12/2007 | Kolatkar .............. | A61K 9/5026 514/448 |
| 2008/0139653 A1 | 6/2008 | Mickle et al. | |
| 2009/0013768 A1 | 1/2009 | Pouteau et al. | |
| 2009/0136980 A1 | 5/2009 | Bebbington et al. | |
| 2009/0137618 A1 | 5/2009 | Jenkins et al. | |
| 2009/0192093 A1 | 7/2009 | Mickle et al. | |
| 2009/0209569 A1 | 8/2009 | Arnelle et al. | |
| 2009/0324710 A1* | 12/2009 | Glidden .................. | A61P 37/02 424/464 |
| 2010/0015249 A1 | 1/2010 | Uwagawa | |
| 2010/0022792 A1 | 1/2010 | Shen | |
| 2010/0035826 A1 | 2/2010 | Jenkins et al. | |
| 2010/0080797 A1 | 4/2010 | Yeomans et al. | |
| 2010/0092562 A1 | 4/2010 | Hollenbeck et al. | |
| 2010/0227921 A1 | 9/2010 | Franklin et al. | |
| 2010/0267614 A1 | 10/2010 | Jenkins | |
| 2010/0286186 A1 | 11/2010 | Franklin et al. | |
| 2011/0159073 A1 | 6/2011 | de Juan et al. | |
| 2011/0262355 A1 | 10/2011 | Jenkins et al. | |
| 2011/0262359 A1 | 10/2011 | Jenkins et al. | |
| 2011/0262360 A1 | 10/2011 | Jenkins et al. | |
| 2011/0281886 A1 | 11/2011 | Jenkins et al. | |
| 2012/0178772 A1 | 7/2012 | Jenkins et al. | |
| 2012/0178773 A1 | 7/2012 | Jenkins et al. | |
| 2012/0230916 A1 | 9/2012 | Jenkins et al. | |
| 2012/0232066 A1 | 9/2012 | Jenkins et al. | |
| 2012/0270847 A1 | 10/2012 | Franklin et al. | |
| 2013/0022671 A1 | 1/2013 | Glidden et al. | |
| 2013/0059914 A1 | 3/2013 | Jenkins et al. | |
| 2013/0210700 A1 | 8/2013 | Jenkins et al. | |
| 2013/0210701 A1 | 8/2013 | Jenkins et al. | |
| 2013/0210854 A1 | 8/2013 | Jenkins et al. | |
| 2014/0121152 A1 | 5/2014 | Jenkins et al. | |
| 2014/0154313 A1 | 6/2014 | Counts et al. | |
| 2014/0206597 A1 | 7/2014 | Jenkins et al. | |
| 2015/0031635 A1 | 1/2015 | Jenkins et al. | |
| 2018/0085366 A1 | 3/2018 | Jenkins et al. | |
| 2022/0287992 A1* | 9/2022 | Kirkpatrick .......... | A61K 9/1623 |

FOREIGN PATENT DOCUMENTS

| | | |
|---|---|---|
| EP | 1782834 | 5/2007 |
| EP | 2433655 | 2/2008 |
| GB | 1425099 | 2/1976 |
| JP | H 0940579 | 2/1997 |
| WO | WO 1997012903 | 4/1997 |
| WO | WO 2002043767 | 6/2002 |
| WO | WO 2004082620 | 9/2004 |
| WO | WO 2005032474 | 4/2005 |
| WO | WO 2005042772 | 5/2005 |
| WO | WO 2007022535 | 2/2007 |
| WO | WO 2007120648 | 10/2007 |
| WO | WO 2007120864 | 10/2007 |
| WO | WO 2007140272 | 12/2007 |
| WO | WO 2008012046 | 1/2008 |
| WO | WO 2008101187 | 8/2008 |
| WO | WO 2008101202 | 8/2008 |
| WO | WO 2009067703 | 5/2009 |
| WO | WO 2009080030 | 7/2009 |
| WO | WO 2009092073 | 7/2009 |
| WO | WO 2009136392 | 11/2009 |
| WO | WO 2010045599 | 4/2010 |
| WO | WO 2010100477 | 9/2010 |
| WO | WO 2010148305 | 12/2010 |
| WO | WO 2011007247 | 1/2011 |
| WO | WO 2011031350 | 3/2011 |
| WO | WO 2011133346 | 4/2011 |
| WO | WO 2011133149 | 10/2011 |
| WO | WO 2011133178 | 10/2011 |
| WO | WO 2011133347 | 10/2011 |
| WO | WO 2011133348 | 10/2011 |
| WO | WO 2012122422 | 9/2012 |
| WO | WO 2020181000 | 9/2020 |

OTHER PUBLICATIONS

Naiserova et al. "(Meth)acrylate copolymers of Eudragit® type in oral tablet technology" Ces.slov. Farm. 2019;68, 183-197 (Year: 2019).*

Bak et al. (1999) "Acyloxyalkoxy-Based Cyclic Prodrugs of Opioid Peptides: Evaluation of the Chemical and Enzymatic Stability as Well as Their Transport Properties Across Caco-2 Cell Monolayers" *Pharm Res* 16(1):24-29.

Bernkop-Schnurch (1998) "The use of inhibitory agents to overcome the enzymatic barrier to perorally administered therapeutic peptides and proteins" *J Control Release* 50(1-2):1-16.

Bioavailability and Bioequivalence Studies for Orally Administered Drug Products—General Considerations, Guidance for Industry, Food and Drug Administration, published on Oct. 2000.

Birk et al. (1976) "Trypsin and chymotrypsin inhibitors from soybeans" *Methods in Enzymology* 45:700-707.

Camostat Medilate (http://www.scbt.com/datasheet-203867-camostat-messylate.html (downloaded on Nov. 14, 2013).

Danziger and Dean; (1989) "Automated site-directed drug design: a general algorithm for knowledge acquisition about hydrogen-bonding regions at protein surfaces"; Proc R Soc Lond B Biol Sci. 236(1283); pp. 101-113.

(56) References Cited

OTHER PUBLICATIONS

Database Internet [Online] Apr. 5, 2005 (Apr. 5, 2005), XP002350634 retrieved from Internet accession No. http://onlineethics.org/reseth/helsinki.html.
Database Registry (2001) Abstract, Database accession No. 339089-42-8; 1 page.
De Nardo et al. (1977) "Studies on chemical structure and sweet taste. Note XIII. L-Acylamidosuccinilic acid derivatives" Database Caplus, Abstract, Database accession No. 1977:119365; 1 page.
Definition of "ex vivo" from thefreedictionary.com, accessed Oct. 7, 2014.
Geratz et al. (1976) "Novel bis(benzamidine) compounds with an aromatic central link. Inhibitors of thrombin, pancreatic kallikrein, trypsin, and complement" *J. Med. Chem.* 19:634-639.
Göke et al. (1984) "Effect of a Specific Serine Protease Inhibitor on the Rat Pancreas: Systemic Administration of Camostate and Exocrine" *Digestion* 30:171-178.
Gomes et al. (2007) "Cyclization-activated prodrugs" *Molecules* 12:2484-2506.
Gotoh et al. (2005) "The advantages of the Ussing chamber in drug absorption studies" *Journal of Biomolecular Screening* 10(5):517-523.
Gottschalk, et al., (2001), "New Concepts inAcute Pain Therapy: Preemptive Analgesia", American Family Physician, 63(10):1979-1984.
Hansch et al. (1990) "Comprehensive Medicinal Chemistry, vol. 5 Biopharmaceutics" *Rational Design, Mechanistic Study And Therapeutic Application Of Chemical Compounds, Oxford, Pergamon Press* 5:251-278.
Hijikata-Okunomiya et al. (2000) "Selective Inhibition of Trypsin by (2R,4R)-4-Phenyl-1-1-[$N^{\alpha}$-(7-methoxy-2-naphthalenesulfonyl)-L-arginy1]-2-piperidinecarboxylic Acid" *J. Biochem.* 275:18995-18999.
Hyams "Medical Conditions: Abdominal Pain, Recurrent" (downloaded on Nov. 21, 2014 from URL: http://www.pediatricweb.com/webpost/iframe/MedicalConditions_465.asp?tArticleId=94 ) 4 pages.
Iwanowicz et al. (2002) "Retro-Binding Thrombin Active Site Inhibitors: Identification of an Orally Active Inhibitor of Thrombin Catalytic Activity" *Bioorganic and Medicinal Chemistry Letters* 12:3183-3186.
Katragadda et al. (2006) "Simultaneous Modulation of Transport and Metabolism of Acyclovir Prodrugs across Rabbit Cornea: An approach Involving Enzyme Inhibitors" *Int J Pharm* 320(1-2):104-113.
Kunze et al. (1983) "Effects of the serine protease inhibitors FOY and FOY 305 on phospholipase A I (EC 3.1.1.32) activity in rat-liver lysosomes" *Pharm. Research Com.* 15: 451-459.
Lapidus and Sweeney (1973) "L-4'-Cyano-3-(2.2.2-trifluoroacetamideo)s uccinanilic Acid and Related Synthetic Sweetening Agents" *J. Med. Chem.* 16(2):163-166.
Lin et al. (1993) "The 0.25-nm X-ray structure of the Bowman-Birk type inhibitor from mung bean in ternary complex with porcine trypsin" *Eur. J. Biochem.* 212:549-555.
Markwardt et al. (1968) "Comparative studies on the inhibition of trypsin, plasmin, and thrombin by derivatives of benzylamine and benzylamidine" *Eur. J. Biochem*, 6:502-506.
Nafamostat (PubChem, National Center for Biotechnology Information dated Dec. 20, 2005).
Nechab et al. (2008) "N-Acylglycinates as acyl donors in serine protease-catalyzed kinetic resolution of amines. Improvement of selectivity and reaction rates." *Org. Biol. Chem.* 6:3917-3920.
Opiois911 (downloaded on Nov. 21, 2014 from URL: http://opioids911.org/safety.php ).
Ozawa et al. (1966) "The reactive site of trypsin inhibitors" *J. Biol. Chem.* 241:3955-3961.
Pain Doctor, "Phantom Limb Pain", (downloaded on Nov. 21, 2014 from URL: http://paindoctor.com/conditions/common/phantom-limb-pain/).
Pauletti, Giovanni et al. (1997) "Esterase-Sensitive Cyclic Prodrugs of Peptides: Evaluation of a Phenylpropionic Acid Promoiety in a Model Hexapeptide" *Pharm Res* 14(1):11-17.
Perona et al. (1995) "Structural basis of substrate specificity in the serine proteases"; Protein Science vol. 4; pp. 337-360.
Plummer et al. (1997) "Design of peptidomimetic ligands for the pp60srcSH2 domain" *Bioorganic and Medicinal Chemistry* 5(1):41-47.
Prater et al. (2002) "Successful Pain Management for the Recovering Addicted Patient" *Primary Care Companion J Clin Psychiatry* 4(4):125-131.
Ramjee et al. (2000) "The Kinetic and Structural Characterization of the Reaction of Nafamostat with Bovine Pancreatic Trypsin" *Thrmb Res.* 98(6):559-569.
Reddy et al. (2012) "An improved process for the preparation of lisdexamfetamine and its pharmaceutically acceptable salts" Database Caplus, Abstract, Database accession No. 2012:654913.
Renatus et al. (1998) "Structural and Functional Analyses of Benzamidine-Based Inhibitors in Complex with Trypsin: Implications for the Inhibition of Factor Xa, tPA, and Urokinase" *J. Med. Chem.* 41(27):5445-5456.
Schanker et al. (1958) "Absorption of drugs from the rat small intestine" *Journal of Pharmacology and Experimental Therapeutics* 123(1):81-88.
Senoo et al. (1966) "Glutamic acid amides" Database Caplus, Abstract, Database accession No. 1966:19804.
Simone Joseph; "Oncology (Introduction)" Textbook of Medicine, 20(1), pp. 1004-1010 (Year: 1997).
Song, Xiaoping et al. (2002) "Synthesis of a Novel Cyclic Prodrug of RGD Peptidomimetic to Improve Its Cell Membrane Permeation" *Bioorg Chem* 30(4):285-301.
Tanizawa et al. (1987) "Inverse Substrates for Tryspin and Tryspin-like Enzymes" *Acc. Chem. Res.* 20:337-343.
Testa et al. (2003) "Hydrolysis in Drug and Prodrug Metabolism" Verlag Helvetica Chimica Acta, Postfach, CH-8042, Switzerland, pp. 420-534.
Tirkkonen et al. (2004) "Drug interactions with the potential to prevent prodrug activation as a common source of irrational prescribing in hospital inpatients" *Clinical Pharmacology and Therapeutics* 76(6):639-647.
Umezawa (1976) "Structure and activities of protease inhibitors of microbial origin" *Methods in Enzymology* 45:678-695.
Van Gelder et al. (2002) "Intestinal absorption enhancement of the ester prodrug tenofovir disoproxil fumarate through modulation of the biochemical barrier by defined ester mixtures" *Drug Metabolism and Disposition* 30(8):924-930.
Ishizaki, et al (2008) "Nafamostat Mesilate, a Potent Serine Protease Inhibitor, Inhibits Airway Eosinophilic Inflammation and Airway Epithelial Remodeling in a Murine Model of Allergic Asthma"; J Pharmacol Science, 108(3); pp. 355-363.
Yin, et al (2006) "Properties of poly(lactic-co-glycolic acid) nanospheres containing protease inhibitors: Camostat mesilate and nafamostat mesylate"; International Journal Of Pharmaceutics, Elsevier, Amsterdam, NL; vol. 314, No. 1, 11; pp. 46-55; XP027972308.

* cited by examiner

5% weight gain

MODIFIED RELEASE COMPOSITIONS OF NAFAMOSTAT AND METHODS OF USING SAME

CROSS-REFERENCE TO RELATED APPLICATION

This application is related to U.S. Provisional Patent Application Ser. No. 63/158,654 filed Mar. 9, 2021; the disclosure of which application is herein incorporated by reference.

INTRODUCTION

Drug abuse, such as prescription opioid abuse, addiction and overdose are major burdens to patients and society, resulting in significant costs, illnesses, and deaths. To avoid these detrimental effects of drug abuse, pharmaceutical compositions that specifically reduce the chances of drug overdose, particularly, even after overdose of such drugs by a subject, are desired.

SUMMARY

The present disclosure provides pharmaceutical compositions (e.g., orally administered), and their methods of use, where the pharmaceutical compositions comprise nafamostat or a pharmaceutically acceptable salt thereof and provide controlled release of nafamostat or pharmaceutically acceptable salt thereof for an extended period of time. In some embodiments, the nafamostat or pharmaceutically acceptable salt thereof is present in the composition in an amount sufficient to inhibit one or more gastrointestinal (GI) enzymes, such as, trypsin. In certain embodiments, the controlled release nafamostat composition provides controlled release of nafamostat to a subject for a duration of 12 hours or more, such as for 24 hours or more.

In certain instances, the controlled release compositions of nafamostat or a pharmaceutically acceptable salt thereof comprise a plurality of controlled release beads, each bead comprising: a core, an active agent layer comprising nafamostat or a pharmaceutically acceptable salt thereof and a controlled release layer comprising one or more polymers formulated in an amount sufficient to provide for controlled release of the nafamostat or pharmaceutically acceptable salt thereof. In some embodiments, the plurality of beads are encapsulated in a capsule.

In some embodiments, the core is formed from one or more polysaccharides. In some instances, the core is formed from a cellulose polymer. In certain instances, the core is formed from microcrystalline cellulose.

In some embodiments, the active agent layer includes nafamostat or a pharmaceutically acceptable salt thereof. In some instances, the active agent layer includes nafamostat free base. In some instances, the active agent layer includes a pharmaceutically acceptable salt of nafamostat. In certain instances, the active agent layer includes nafamostat mesylate.

In some embodiments, the active agent layer includes a binder. In some instances, the binder is a water-soluble film-forming polymer. In certain instances, the soluble film-forming polymer is a polysaccharide, such as a water-soluble cellulose polymer. In certain embodiments, the active agent layer includes hydroxypropylmethylcellulose.

The controlled release layer can include one or more acrylate polymers, methacrylate polymers, a copolymer of one or more acrylate polymers or methacrylate polymers or a combination thereof. In some embodiments, the controlled release layer includes an acrylate copolymer formed from monomers of ethylacrylate, methyl-methacrylate and chlorotrimethyl-ammonioethyl methacrylate. In certain instances, the controlled release layer includes poly(ethylacrylate, methyl-methacrylate and chlorotrimethyl-ammonioethyl methacrylate). The poly(ethylacrylate, methyl-methacrylate and chlorotrimethyl-ammonioethyl methacrylate) can contain different amounts of quaternary ammonium groups, for example, about 50 mEq of quaternary ammonium groups per 100 g of polymer (acrylate copolymer A) or about 25 mEq of quaternary ammonium groups per 100 g of polymer (acrylate copolymer B). Beads containing controlled release layers having different ratios of acrylate copolymer B and acrylate copolymer A are provided. For example, the controlled release layer can contain between 5% and 100% of acrylate copolymer B and between 5% and 100% of acrylate copolymer A. In certain embodiments, the controlled release layer includes a ratio of acrylate copolymer B to acrylate copolymer A of 80:20, such as a ratio of acrylate copolymer B to acrylate copolymer A of 87:13, such as a ratio of acrylate copolymer B to acrylate copolymer A of 90:10, such as a ratio of acrylate copolymer B to acrylate copolymer A of 92:8 and including a ratio of acrylate copolymer B to acrylate copolymer A of 95:5.

In certain embodiments, compositions of interest can further comprise nafamostat or a pharmaceutically acceptable salt thereof in an immediate release form that provides for immediate release of the nafamostat or pharmaceutically acceptable salt thereof to a subject. In some instances, immediate release nafamostat or pharmaceutically acceptable salt thereof is present in the oral composition as a powder or granulate. In some instances, immediate release nafamostat or pharmaceutically acceptable salt thereof is present in the oral composition as an immediate release layer coated on top of the controlled release layer of the plurality of beads.

Aspects of the present disclosure also include methods for administering (e.g., orally) to a subject in need thereof one or more of the compositions described herein. In some embodiments, administering the composition is sufficient to provide for sustained release of one or more doses of nafamostat or a pharmaceutically acceptable salt thereof to the subject over an extended period of time, such as for 12 hours or longer, including for 24 hours or longer. In some instances, administering the composition is sufficient to provide for a delayed immediate release of one or more doses of nafamostat or a pharmaceutically acceptable salt thereof to the subject. In certain instances, administering the composition is sufficient to provide an immediate dose of the nafamostat or a pharmaceutically acceptable salt thereof to the subject followed by sustained release of nafamostat or a pharmaceutically acceptable salt thereof to the subject over an extended period of time. In certain instances, administering the composition is sufficient to provide a first immediate dose of the nafamostat or a pharmaceutically acceptable salt thereof to the subject followed by a second immediate release dose of the nafamostat or a pharmaceutically acceptable salt thereof to the subject at a predetermined time after the first immediate dose.

DETAILED DESCRIPTION

Figure 1:
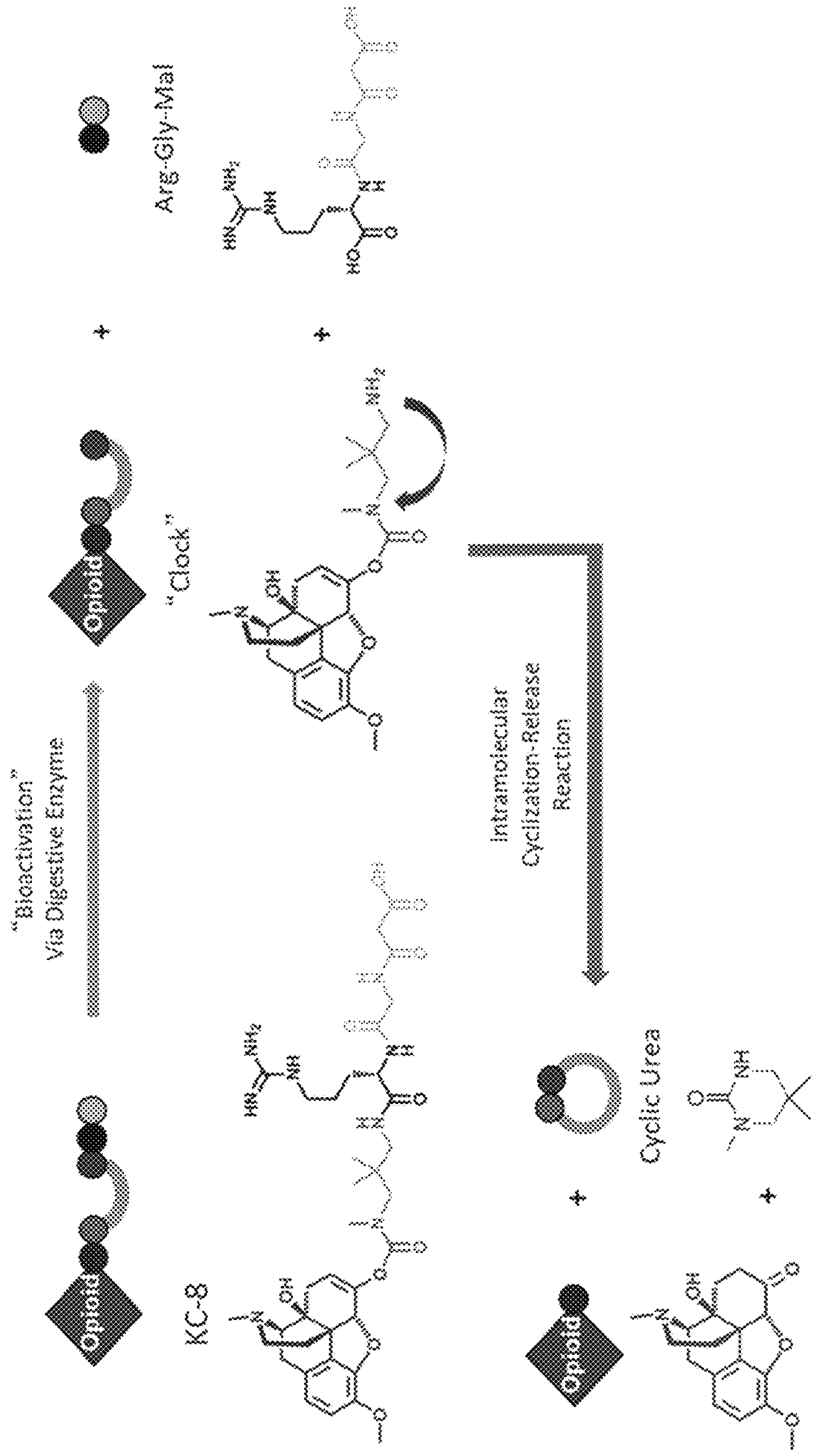
FIG. 1 shows a biochemical mechanism wherein an oxycodone derivative is converted into active oxycodone by action of a digestive enzyme such as trypsin.

Aspects of the present disclosure include a composition of nafamostat or a pharmaceutically acceptable salt thereof that provides for controlled release of nafamostat or pharmaceutically acceptable salt thereof to a subject for an extended period of time. Compositions according to certain embodiments include a plurality of controlled release beads where each bead includes a core, an active agent layer having nafamostat or a pharmaceutically acceptable salt thereof and a controlled release layer having one or more polymers formulated in an amount sufficient to provide for controlled release of the nafamostat or pharmaceutically acceptable salt thereof. Methods for administering (e.g., orally or through the respiratory system) the controlled release nafamostat compositions to a subject are also described.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

As used herein, the singular forms “a”, “an,” and “the” are intended to include the plural forms as well, unless the context clearly indicates otherwise. Furthermore, to the extent that the terms “including,” “includes,” “having,” “has,” “with,” or variants thereof are used in either the detailed description and/or the claims, such terms are intended to be inclusive in a manner similar to the term “comprising.” The transitional terms/phrases (and any grammatical variations thereof) “comprising,” “comprises,” “comprise,” “consisting essentially of,” “consists essentially of,” “consisting,” and “consists” can be used interchangeably.

The term “about” or “approximately” means within an acceptable error range for the particular value as determined by one of ordinary skill in the art, which will depend in part on how the value is measured or determined, i.e., the limitations of the measurement system. In the context of compositions containing amounts of ingredients where the terms “about” or “approximately” are used, these compositions contain the stated amount of the ingredient with a variation (error range) of 0-10% around the value (X±10%).

In the present disclosure, ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. Values having at least two significant digits within a range are envisioned, for example, a range of 5-10 indicates all the values between 5.0 and 10.0 as well as between 5.00 and 10.00 including the terminal values.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

Compositions of Nafamostat or a Pharmaceutically Acceptable Salt Thereof

As summarized above, aspects of the present disclosure include a composition of nafamostat or a pharmaceutically acceptable salt thereof that provides for controlled release of nafamostat or pharmaceutically acceptable salt thereof to a subject for an extended period of time. As described herein, the compound nafamostat refers to 6-carbamimidoylnaphthalen-2-yl 4-(diaminomethyleneamino)benzoate:

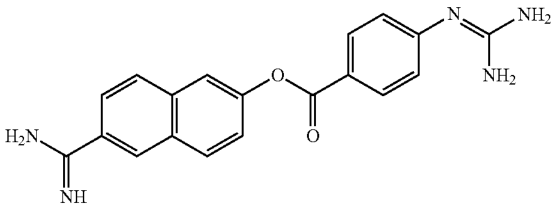

Nafamostat (6-carbamimidoylnaphthalen-2-yl 4-(diaminomethyleneamino)benzoate)

In some embodiments, compositions include nafamostat free base. In other embodiments, compositions include a pharmaceutically acceptable salt of nafamostat. In embodiments, "salts" of nafamostat may include, but are not limited to: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the compound is replaced by a metal ion, e.g., an alkali metal ion, an alkaline earth ion, or an aluminum ion; or coordinates with an organic base such as ethanolamine, diethanolamine, triethanolamine, N-methylglucamine and the like. In certain embodiments, the salt of nafamostat is nafamostat mesylate.

The term "solvate" as used herein refers to a complex or aggregate formed by one or more molecules of a solute and one or more molecules of a solvent. Such solvates may be crystalline solids having a substantially fixed molar ratio of solute and solvent. Representative solvents include by way of example, water, methanol, ethanol, isopropanol, acetic acid, and the like. When the solvent is water, the solvate formed is a hydrate.

In embodiments, compositions of nafamostat or a pharmaceutically acceptable salt thereof provide post administration-activated, controlled release of nafamostat or pharmaceutically acceptable salt thereof to a subject for an extended period of time. In some embodiments, compositions described herein are orally administered compositions. In some embodiments, compositions are formulated for administering to the respiratory system of the subject (e.g., through inhalation).

In some embodiments, the controlled release composition provides for the sustained release of one or more doses of nafamostat or pharmaceutically acceptable salt thereof to the subject. In some instances, the sustained release of nafamostat is a zero-order sustained release. In other instances, the sustained release of nafamostat is a first-order sustained release. For example, controlled release nafamostat compositions may provide for sustained release of 0.000001 μg/min or more of the nafamostat, such as 0.000005 μg/min or more, such as 0.00001 μg/min or more, such as 0.0005 μg/min or more, such as 0.001 μg/min or more, such as 0.005 μg/min or more, such as 0.01 μg/min or more, such as 0.05 μg/min or more, such as 0.1 μg/min or more, such as 0.5 μg/min or more, such as 1 μg/min or more, such as 5 μg/min or more, such as 10 μg/min or more, such as 100 μg/min or more and including sustained release of 250 μg/min or more of nafamostat or pharmaceutically acceptable salt thereof.

In some embodiments, controlled release compositions of nafamostat provide for delayed immediate release of nafamostat or pharmaceutically acceptable salt thereof. The term "delayed immediate release" is used herein to refer to the timing that nafamostat or pharmaceutically acceptable salt thereof is released after administration, where an amount of the nafamostat is released from the composition at a predetermined period of time after administration to the subject. In some instances, delayed immediate release compositions of nafamostat are formulated to release 50% or more of nafamostat or pharmaceutically acceptable salt thereof at the predetermined period of time, such as formulated to release 60% or more, such as 70% or more, such as 80% or more, such as 90% or more, such as 95% or more, such as 97% or more, such as 99% or more and including being formulated to release all of the nafamostat in the composition (100%) at a predetermined period of time after administration of the composition to the subject. The period of time of the delayed release may vary, where in some instances, compositions of interest are formulated to release the nafamostat or pharmaceutically acceptable salt thereof 5 minutes or more after orally administering the composition to the subject, such as 10 minutes or more, such as 15 minutes or more, such as 20 minutes or more, such as 30 minutes or more, such as 45 minutes or more, such as 60 minutes or more, such as 2 hours or more, such as 3 hours or more, such as 4 hours or more, such as 6 hours or more, such as 8 hours or more, such as 10 hours or more, such as 12 hours or more, such as 18 hours or more and including 24 hours or more after orally administering the composition to the subject.

In some embodiments, the controlled release compositions of nafamostat provide for a release profile where 50% or more of the nafamostat or pharmaceutically acceptable salt thereof is released within 6 hours after administration, such as 55% or more, such as 60% or more, such as 65% or more, such as 70% or more, such as 75% or more, such as 80% or more, such as 85% or more, such as 90% or more, such as 95% or more, such as 97% or more such as 99% or more and including being formulated to release all of the nafamostat in the composition (100%) within 6 hours after administration of the composition to the subject.

In certain embodiments, the controlled release compositions provide for release of nafamostat or pharmaceutically acceptable salt thereof at a first rate for a first predetermined period of time followed by releasing the nafamostat or pharmaceutically acceptable salt thereof at a second rate for a second predetermined period of time. In some instances, the controlled release composition is configured to release nafamostat at rate of 0.000001 μg/min or more for a first predetermined period of time, such as 0.000005 μg/min or more, such as 0.00001 μg/min or more, such as 0.0005 μg/min or more, such as 0.001 μg/min or more, such as 0.005 μg/min or more, such as 0.01 μg/min or more, such as 0.05 μg/min or more, such as 0.1 μg/min or more, such as 0.5 μg/min or more, such as 1 μg/min or more, such as 5 μg/min or more, such as 10 μg/min or more, such as 100 μg/min or more and including releasing 250 μg/min or more for a first predetermined period of time. In some instances, the first predetermined period of time is 5 minutes or more, such as 10 minutes or more, such as 15 minutes or more, such as 20 minutes or more, such as 30 minutes or more, such as 45 minutes or more, such as 60 minutes or more, such as 2 hours or more, such as 3 hours or more, such as 4 hours or more, such as 6 hours or more, such as 8 hours or more, such as 10 hours or more, such as 12 hours or more, such as 18 hours or more and including 24 hours or more. In some instances, the first period of time is followed by controlled release of nafamostat at rate of 0.000001 μg/min or more for a second predetermined period of time, such as 0.000005 μg/min or more, such as 0.00001 μg/min or more, such as 0.0005 μg/min or more, such as 0.001 μg/min or more, such as 0.005 μg/min or more, such as 0.01 μg/min or more, such as 0.05 μg/min or more, such as 0.1 μg/min or more, such as 0.5 μg/min or more, such as 1 μg/min or more, such as 5 μg/min or more, such as 10 μg/min or more, such as 100 μg/min or more and including 250 μg/min or more for a second predetermined period of time. In some instances, the second predetermined period of time is 30 minutes or more, such as 60 minutes or more, such as 2 hours or more, such as 3 hours or more, such as 4 hours or more, such as 6 hours or more, such as 8 hours or more, such as 12 hours or more, such as 24 hours or more, such as 48 hours or more and including 72 hours or more.

In certain embodiments, compositions of nafamostat or a pharmaceutically acceptable salt thereof are formulated as a plurality of controlled release beads where each bead includes a core, an active agent layer having nafamostat or a pharmaceutically acceptable salt thereof and a controlled release layer having one or more polymers formulated in an amount sufficient to provide for controlled release of the nafamostat or pharmaceutically acceptable salt thereof. In some embodiments, the size of the beads ranges from 0.001 mm to 5 mm in diameter, such as from 0.005 mm to 4.5 mm, such as from 0.01 mm to 4 mm, such as from 0.05 mm to 3.5 mm, such as from 0.1 mm to 3 mm, such as from 0.5 mm to 2.5 mm, such as from 1 mm to 3 mm and including from 0.2 mm and 3 mm in diameter.

In some instances, the core is formed from an inert substance. Such substances include a cellulose polymer, silicon dioxide, a sugar, starch, or a combination thereof. The sugar can be glucose, sucrose, lactose, mannitol, xylitol, sorbitol, or a combination thereof. In some embodiments, the core may be formed from microcrystalline cellulose, Cellets® cores, such as Cellets® 100, Cellets® 200, Cellets® 350, Cellets® 500, Cellets® 700, or Cellets® 1000 (Glatt Air Techniques Inc., Ramsey N.J.). In other embodiments, the core is prepared de novo, for example by preparing a polymer mixture, extruding the mixture, and spheronizing the extruded mixture to form spherical or semi-spherical beads. In some embodiments, the beads are swellable such that their exposure to aqueous media causes them to swell and release the active ingredient rapidly and efficiently. In some embodiments, the core comprises between about 10% to about 50% of the total weight of the finally-formulated bead. In some embodiments, the core comprises between about 15% to about 40% of the total weight of the finally-formulated bead. In some embodiments, the core comprises between about 20% to about 30% of the total weight of the finally-formulated bead. In some embodiments, the core comprises about 20% of the total weight of the finally-formulated bead. In some embodiments, the core comprises about 25% of the total weight of the finally-formulated bead. In certain embodiments, the core is a microcrystalline cellulose (MCC) bead, such as a Cellets microcrystalline cellulose bead.

In some embodiments, an active agent layer having nafamostat or a pharmaceutically acceptable salt thereof (e.g., nafamostat or nafamostat mesylate) is formed on the core. In some embodiments, the active agent layer comprises between about 1% to about 50% of the total weight of the bead. In some embodiments, the active agent layer comprises between about 2% to about 40% of the total weight of the bead. In some embodiments, the active agent layer comprises between about 5% to about 30% of the total weight of the bead. In some embodiments, the active agent layer comprises between about 7% to about 25% of the total weight of the bead. In some embodiments, the active agent layer comprises between about 8% to about 15% of the total weight of the bead. In some embodiments, the active agent layer comprises about 8% of the total weight of the bead. In some embodiments, the active agent layer comprises about 10% of the total weight of the bead. In some embodiments, the active agent layer comprises about 12% of the total weight of the bead. In some embodiments, the active agent layer comprises about 15% of the total weight of the bead.

In some embodiments, the application of the active agent layer causes a weight gain of between about 1% to about 50% of the weight prior to the application of the active agent layer. Thus, for example, if the weight of the core prior to the application of the active agent layer is X, then after the application of the active agent layer, the weight of each bead is 1.01×, if the weight gain is 1%, or the weight of each bead is 1.5×, if the weight gain is 50%. In some embodiments, the weight gain is between about 5% to about 45%. In some embodiments, the weight gain is between about 5% to about 40%. In some embodiments, the weight gain is between about 5% to about 35%. In some embodiments, the weight gain is between about 5% to about 30%. In some embodiments, the weight gain is between about 10% to about 25%.

Nafamostat or a pharmaceutically acceptable salt thereof may be present in the active agent layer of each bead in an amount of 0.000001 mg or more, such as 0.00001 mg or more, such as 0.0001 mg or more, such as 0.001 mg or more, such as 0.01 mg or more, such as 0.1 mg or more, such as 0.5 mg or more, such as 1 mg or more and including 2 mg or more. In some embodiments, the drug loading of nafamostat or pharmaceutically acceptable salt thereof of each bead is from 1% w/w to 25% w/w, such as from 2% w/w to 24% w/w, such as from 3% w/w to 23% w/w, such as from 4% w/w to 22% w/w, such as from 5% w/w to 21% w/w, such as from 6% w/w to 20% w/w, such as from 7% w/w to 19% w/w, such as from 8% w/w to 18% w/w, such as from 9% w/w to 15% w/w and including from 11% w/w to 13% w/w. As described in greater detail below, oral compositions of nafamostat according to embodiments of the present disclosure may include 10 mg or more of nafamostat or a pharmaceutically acceptable salt thereof, such as 15 mg or more, such as 20 mg or more, such as 25 mg or more, such as 30 mg or more, such as 35 mg or more, such as 40 mg or more, such as 45 mg or more, such as 50 mg or more, such as 60 mg or more, such as 70 mg or more, such as 80 mg or more, such as 90 mg or more, such as 100 mg or more, such as 150 mg or more and including 200 mg or more.

In addition to nafamostat or a pharmaceutically acceptable salt thereof, the active agent layer can further contain a binder. The binder can be a pharmaceutically acceptable polymer, such as a hydroxyalkyl cellulose, maltodextrin, cellulose acetate phthalate, sucrose, modified starch, a salt of alginic acid, soluble gums, carrageenan, an alkyl cellulose, corn starch, polyethylene glycol, polyethylene oxide, hydroxypropylmethylcellulose phthalate, insoluble gums, polymethacrylate, polyvinylpyrrolidone (PVP) or polyvinylpolypyrrolidone (PVPP), polyvinyl alcohol, shellac, and polyvinyl acetate phthalate or any combination thereof. A hydroxyalkyl cellulose can be hydroxypropyl cellulose, hydroxyethyl cellulose, hydroxypropylmethyl cellulose, or any combination thereof. An alkyl cellulose can be cellulose, ethyl cellulose, ethylmethyl cellulose, or any combination thereof. In certain embodiments, the binder comprises hydroxypropyl methylcellulose.

In some embodiments, the active agent layer containing nafamostat or a pharmaceutically acceptable salt thereof may further include a de-tackifier or glidant, such as talc, an amorphous silica such as syloid (e.g., syloid 244FP), a monoglyceride, a diglyceride, glyceryl monostearate, calcium stearate, and magnesium stearate.

In other embodiments, the active agent layer containing the nafamostat or a pharmaceutically acceptable salt thereof includes a lipid excipient, such as glyceryl behenate, glycerol esters of fatty acids, glyceryl dibehenate, behenoyl macrogoglycerides, glyceryl distearate, glycerol distearate, glyceryl palmitostearate, lauroyl macrogoglycerides, stearoyl macrogoglycerides, abitec products, glyceryl monooleate, medium chain mono-& diglycerides, glyceryl monocaprylate, glyceryl tricaprylate/caprate/stearate, hydrogenated vegetable oil, hydrogenated cottonseed oil, hydrogenated soybean oil, hydrogenated soybean oil and castor wax, polyoxyethylene 8 caprylic/capric glycerides, polyoxyethylene 6 caprylic/capric glycerides, polyoxyethylene 32 lauric glycerides, polyoxyethylene 6 prop. Glycol esters, polyoxyethylene 7 coconut glycerides, polyoxyethylene 30 coconut glycerides, polyoxyethylene 80 coconut glycerides, polyoxypropylene 15 stearyl ether, polyoxyethylene 26 glyceryl ether, polyoxyethylene 35 soybean glycerides, polyoxyethylene 20 sorbitol, polyoxypropylene myristyl ether, polyoxypropylene 10 cetostearyl ether, palm kernelamide diethanolamide, triglycerol mono-oleate, sasol products, hydrogenated coco-glycerides, cetyl palmitate, trimyristin, tripalmitin, tristearin, hydrogenated palm oil, glyceryl monostearate, glyceryl stearate, cetearyl alcohol, cetyl alcohol, capric triglyceride, acetylated glycerides, glyceryl cocoate, and polyethylene glycol or combinations thereof.

In certain embodiments, the active agent layer containing nafamostat or a pharmaceutically acceptable salt thereof includes nafamostat or a pharmaceutically acceptable salt thereof and hydroxypropyl methylcellulose.

In some embodiments, the controlled release beads include a controlled release layer having one or more polymers formulated to provide for controlled release of the nafamostat or pharmaceutically acceptable salt thereof. The polymers are pharmaceutically acceptable and suitable for providing controlled release of nafamostat over an extended period of time as described above. In some instances, polymers of the controlled release layer include but are not limited to cellulose ethers such as Ethocel™, acrylate polymers, methacrylate polymers, neutral (meth)acrylate-based polymers such as Eudragit™ NE 30D, ionic (meth)acrylate-based polymers such as Eudragit™ RS or RL, polyvinyl acetate, or combinations thereof. In certain embodiments, polymers of the controlled release layer are stabilized with polyvinylpyrrolidone (PVP), such as Kollicoat™ SR.

In some embodiments, the controlled release layer includes an acrylate copolymer. Acrylate copolymers can include copolymers of various monomers, such as "soft" monomers, "hard" monomers or "functional" monomers. The acrylate copolymers can be composed of a copolymer including a bipolymer (i.e., made with two monomers), a terpolymer (i.e., made with three monomers), or a tetrapolymer (i.e., made with four monomers), or copolymers having greater numbers of monomers. The acrylate copolymers may be crosslinked or non-crosslinked. The polymers can be cross-linked by known methods to provide the desired polymers. The monomers from of the acrylate copolymers may include two or more components selected from the group including acrylic acids, alkyl acrylates, methacrylates, copolymerizable secondary monomers or monomers with functional groups. Monomers ("soft" and "hard" monomers) may be methoxyethyl acrylate, ethyl acrylate, butyl acrylate, butyl methacrylate, hexyl acrylate, hexyl methacrylate, 2-ethylbutyl acrylate, 2-ethylbutyl methacrylate, isooctyl acrylate, isooctyl methacrylate, 2-ethylhexyl acrylate, 2-ethylhexyl methacrylate, decyl acrylate, decyl methacrylate, dodecyl acrylate, dodecyl methacrylate, tridecyl acrylate, tridecyl methacrylate, acrylonitrile, methoxyethyl acrylate, methoxyethyl methacrylate, and the like. In certain embodiments, the controlled release layer includes a methacrylate acrylate copolymer or a mixture of two or more methacrylate acrylate copolymers. In some instances, methacrylate acrylate copolymers of interest are substantially the same as Eudragit™ acrylate copolymers, as described below. In certain instances, the controlled release layer includes an acrylate copolymer that is substantially the same as Eudragit RS. In certain instances, the controlled release layer includes an acrylate copolymer that is substantially the same as Eudragit RL. In certain instances, the controlled release layer includes a first acrylate copolymer that is substantially the same as Eudragit RS and a second acrylate copolymer that is substantially the same as Eudragit RL.

In some embodiments, the controlled release layer includes two different polymers (e.g., two different acrylate copolymers). In some instances, the first polymer is present in the controlled release layer in an amount that ranges from 0.01% to 99.99% by weight, such as from 0.1% to 99.9% by weight, such as from 0.5% to 99.5% by weight, such as from 1% to 99% by weight, such as from 2% to 98% by weight, such as from 3% to 97% by weight, such as from 4% to 96% by weight, such as from 5% to 95% by weight, such as from 6% to 94% by weight, such as from 7% to 93% by weight, such as from 8% to 92% by weight, such as from 9% to 91% by weight, such as from 10% to 90% by weight, such as from 15% to 85% by weight, such as from 20% to 80% by weight, such as from 25% to 75% by weight, such as from 30% to 70% by weight, such as from 35% to 65% by weight, such as from 40% to 60% by weight and including from 45% to 55% by weight. In some instances, the second polymer is present in the controlled release layer in an amount that ranges from 0.01% to 99.99% by weight, such as from 0.1% to 99.9% by weight, such as from 0.5% to 99.5% by weight, such as from 1% to 99% by weight, such as from 2% to 98% by weight, such as from 3% to 97% by weight, such as from 4% to 96% by weight, such as from 5% to 95% by weight, such as from 6% to 94% by weight, such as from 7% to 93% by weight, such as from 8% to 92% by weight, such as from 9% to 91% by weight, such as from 10% to 90% by weight, such as from 15% to 85% by weight, such as from 20% to 80% by weight, such as from 25% to 75% by weight, such as from 30% to 70% by weight, such as from 35% to 65% by weight, such as from 40% to 60% by weight and including from 45% to 55% by weight.

The ratio by weight of the first polymer (e.g., first acrylate copolymer) to the second polymer (e.g., second acrylate copolymer) in the controlled release layer may vary, such as from 1:99 to 99:1, such as from 5:95 to 95:5, such as from 10:90 to 90:10, such as from 20:80 to 80:20, such as from 30:70 to 70:30, such as from 40:60 to 60:40 and including where the ratio by weight of the first polymer to the second polymer in the controlled release layer is 50:50. In certain embodiments, the ratio by weight of the first polymer to the second polymer in the controlled release layer may be 80:20, such as the first polymer to the second polymer of 87:13, such as a ratio of the first polymer to the second polymer of 90:10, such as a ratio of the first polymer to the second polymer of 92:8 and including a ratio of the first polymer to the second polymer of 95:5

In some instances, the controlled release layer includes a copolymer of ethylacrylate, methyl methacrylate and chlorotrimethyl-aminonioethyl methacrylate. In certain instances, the polymer is poly(ethylacrylate, methyl-methacrylate and chlorotrimethyl-ammonioethyl methacrylate) containing quaternary ammonium groups. For example, the acrylate copolymer may be a combination of: 1) poly (ethylacrylate, methyl-methacrylate and chlorotrimethyl-ammonioethyl methacrylate) containing about 50 mEq of quaternary ammonium groups per 100 g of polymer (hereinafter, "acrylate copolymer A"; where in some instances, acrylate copolymer A is substantially the same as Eudragit™ RL) and 2) poly(ethylacrylate, methyl-methacrylate and chlorotrimethyl-ammonioethyl methacrylate) containing about 25 mEq of quaternary ammonium groups per 100 g of polymer (hereinafter, "acrylate copolymer B"; where in some instances, acrylate copolymer B is substantially the same as Eudragit™ RS). In some instances, the acrylate copolymer A is present in the polymer of the controlled release layer in an amount that ranges from 0.01% to 99.99% by weight, such as from 0.1% to 99.9% by weight, such as from 0.5% to 99.5% by weight, such as from 1% to 99% by weight, such as from 2% to 98% by weight, such as from 3% to 97% by weight, such as from 4% to 96% by weight, such as from 5% to 95% by weight, such as from 6% to 94% by weight, such as from 7% to 93% by weight, such as from 8% to 92% by weight, such as from 9% to 91% by weight, such as from 10% to 90% by weight, such as from 15% to 85% by weight, such as from 20% to 80% by weight, such as from 25% to 75% by weight, such as from 30% to 70% by weight, such as from 35% to 65% by weight, such as from 40% to 60% by weight and including from 45% to 55% by weight. In some instances, acrylate copolymer B is present in the polymer of the controlled release layer in an amount that ranges from 0.01% to 99.99% by weight, such as from 0.1% to 99.9% by weight, such as from 0.5% to 99.5% by weight, such as from 1% to 99% by weight, such as from 2% to 98% by weight, such as from 3% to 97% by weight, such as from 4% to 96% by weight, such as from 5% to 95% by weight, such as from 6% to 94% by weight, such as from 7% to 93% by weight, such as from 8% to 92% by weight, such as from 9% to 91% by weight, such as from 10% to 90% by weight, such as from 15% to 85% by weight, such as from 20% to 80% by weight, such as from 25% to 75% by weight, such as from 30% to 70% by weight, such as from 35% to 65% by weight, such as from 40% to 60% by weight and including from 45% to 55% by weight.

The ratio by weight of acrylate copolymer A to acrylate copolymer B in the controlled release layer to may vary, such as from 1:99 to 99:1, such as from 5:95 to 95:5, such as from 10:90 to 90:10, such as from 20:80 to 80:20, such as from 30:70 to 70:30, such as from 40:60 to 60:40 and including where the ratio by weight of the acrylate copolymer A to acrylate copolymer B in the controlled release layer is 50:50. In certain embodiments, the controlled release layer includes a ratio of acrylate copolymer B to acrylate copolymer A of 80:20, such as a ratio of acrylate copolymer B to acrylate copolymer A of 87:13, such as a ratio of acrylate copolymer B to acrylate copolymer A of 90:10, such as a ratio of acrylate copolymer B to acrylate copolymer A of 92:8 and including a ratio of acrylate copolymer B to acrylate copolymer A of 95:5.

In certain cases, the polymer of the controlled release layer comprises 20% by weight acrylate copolymer B and 80% by weight acrylate copolymer A.

In certain cases, the polymer of the controlled release layer comprises 50% by weight acrylate copolymer B and 50% by weight acrylate copolymer A.

In certain cases, the polymer of the controlled release layer comprises 80% by weight acrylate copolymer B and 20% by weight acrylate copolymer A.

In certain cases, the polymer of the controlled release layer comprises 100% by weight acrylate copolymer B.

In certain cases, the polymer of the controlled release layer comprises 100% by weight acrylate copolymer A.

In certain cases, the polymer of the controlled release layer comprises 95% by weight acrylate copolymer B and 5% by weight acrylate copolymer A.

In certain cases, the polymer of the controlled release layer comprises 93% by weight acrylate copolymer B and 7% by weight acrylate copolymer A.

In certain cases, the polymer of the controlled release layer comprises 92% by weight acrylate copolymer B and 8% by weight acrylate copolymer A.

In certain cases, the polymer of the controlled release layer comprises 90% by weight acrylate copolymer B and 10% by weight acrylate copolymer A.

In certain cases, the polymer of the controlled release layer comprises 87% by weight acrylate copolymer B and 13% by weight acrylate copolymer A.

In some embodiments, the controlled release layer comprises between about 1% to about 50% of the total weight of the bead. In some embodiments, the controlled release layer comprises between about 2% to about 40% of the total weight of the bead. In some embodiments, the controlled release layer comprises between about 5% to about 30% of the total weight of the bead. In some embodiments, the controlled release layer comprises between about 7% to about 25% of the total weight of the bead. In some embodiments, the controlled release layer comprises between about 8% to about 15% of the total weight of the bead. In some embodiments, the controlled release layer comprises about 8% of the total weight of the bead. In some embodiments, the controlled release layer comprises about 10% of the total weight of the bead. In some embodiments, the controlled release layer comprises about 12% of the total weight of the bead. In some embodiments, the controlled release layer comprises about 15% of the total weight of the bead.

In some embodiments, the application of the controlled release layer causes a weight gain of between about 1% to about 50% of the weight prior to the application of the controlled release layer. Thus, for example, if the weight of the core and active agent layer prior to the application of the controlled release layer is X, then after the application of the controlled release layer, the weight of each bead is 1.01×, if the weight gain is 1%, or the weight of each bead is 1.5×, if the weight gain is 50%. In some embodiments, the weight gain is between about 5% to about 45%. In some embodiments, the weight gain is between about 5% to about 40%. In some embodiments, the weight gain is between about 5% to about 35%. In some embodiments, the weight gain is between about 5% to about 30%. In some embodiments, the weight gain is between about 10% to about 25%, such as 15%.

Certain non-limiting examples of compositions of nafamostat mesylate are provided in Tables 1 and 2 below:

TABLE 1

Composition of Drug Product, Formulations I to IV

| Component | Amount Dose Unit (mg) Formulation I (95:5 RS:RL) | Formulation II (80:20 RS:RL) | Formulation III (80:20 RS:RL) | Formulation IV (95:5 RS:RL) |
|---|---|---|---|---|
| Nafamostat mesylate | 100 | 100 | 1 | 1 |
| Hypromellose capsule | one unit | one unit | one unit | one unit |
| Microcrystalline cellulose spheres | 526.4 | 526.4 | 5.264 | 5.264 |
| Hypromellose | 100 | 100 | 1 | 1 |
| Ammonio methacrylate copolymers type A (Eudragit RL) | 4.5 | 18.1 | 0.181 | 0.045 |
| Ammonio methacrylate copolymers type B (Eudragit RS) | 86.2 | 72.6 | 0.726 | 0.862 |
| Triethyl citrate | 9.1 | 9.1 | 0.091 | 0.091 |
| Talc | 45.4 | 45.4 | 0.454 | 0.454 |
| TOTAL | 871.6 | 871.6 | 8.72 | 8.72 |

Formulation I = High Dose, Slow Release Rate
Formulation II = High Dose, Fast Release Rate
Formulation III = Low Dose, Fast Release Rate
Formulation IV = Low Dose, Slow Release Rate

TABLE 2

Nafamostat Controlled Release Bead Formulations

| | Formulation V (100:0 RS:RL) | Formulation VI (87:13 RS:RL) | Formulation VII (100:0 RS:RL) | Formulaion VIII (93:7 RS:RL) |
|---|---|---|---|---|
| Core | Microcrystalline Cellulose Spheres 63.01% w/w | Microcrystalline Cellulose Spheres 60.3865% w/w | Microcrystalline Cellulose Spheres 60.39% w/w | Microcrystalline Cellulose Spheres 60.3865% w/w |
| Active Agent Layer | Nafamostat 11.97% w/w Hydroxypropyl methylcellulose 11.97% w/w | Nafamostat 11.4734% w/w Hydroxypropyl methylcellulose 11.4734% w/w | Nafamostat 11.47% w/w Hydroxypropyl methylcellulose 11.47% w/w | Nafamostat 11.4734% w/w Hydroxypropyl methylcellulose 11.4734% w/w |

TABLE 2-continued

| Nafamostat Controlled Release Bead Formulations | | | | |
|---|---|---|---|---|
| | Formulation V (100:0 RS:RL) | Formulation VI (87:13 RS:RL) | Formulation VII (100:0 RS:RL) | Formulaion VIII (93:7 RS:RL) |
| Controlled Release Layer | Ammonio methacrylate copolymers type B (Eudragit RSPO) 8.15% w/w Ammonio methacrylate copolymers type A (Eudragit RLPO) 0.0% w/w Triethyl Citrate 0.82% w/w Talc 4.08% w/w | Ammonio methacrylate copolymers type B (Eudragit RSPO) 9.0625% w/w Ammonio methacrylate copolymers type A (Eudragit RLPO) 1.3542% w/w Triethyl Citrate 1.0417% w/w Talc 5.2083% w/w | Ammonio methacrylate copolymers type B (Eudragit RSPO) 10.42% w/w Ammonio methacrylate copolymers type A (Eudragit RLPO) 0.0% w/w Triethyl Citrate 1.04% w/w Talc 5.21% w/w | Ammonio methacrylate copolymers type B (Eudragit RSPO) 9.6875% w/w Ammonio methacrylate copolymers type A (Eudragit RLPO) 0.7292% w/w Triethyl Citrate 10.417% w/w Talc 5.2083% w/w |

In some embodiments, the controlled release layer further includes mold release agents, such as glycerol monostearate. In some embodiments, the controlled release layer also contains one or more plasticizers. In some embodiments, the plasticizer is selected from the group consisting of a phthalate-based plasticizer, a trimellitate, an adipate-based plasticizer, a sebacate-based plasticizer, an organophosphate, a maleate, a sulfonamide, a glycols or polyether, an acetylated monoglyceride, and an alkyl citrate. In certain embodiments, the sebacate-based plasticiser is dibutyl sebacate (DBS). In certain embodiments, the plasticizer is triethyl citrate. In some embodiments, the plasticizer is present in between about 1% to about 20% of the weight of the controlled release layer, or between about 5% to about 15% by weight, or between about 7% to about 10% by weight. In certain embodiments, the controlled release layer can further contain a flavouring agent. In certain cases, the active agent layer and/or the controlled release layer comprise magnesium silicate.

In certain embodiments, the plurality of controlled release beads includes an immediate release layer of nafamostat or pharmaceutically acceptable salt thereof that is coated on top of the controlled release layer. In some instances, the immediate release layer of nafamostat or pharmaceutically acceptable salt thereof is formulated to release 50% or more of the nafamostat or pharmaceutically acceptable salt thereof within 10 minutes or less of administration of the composition to the subject, such as 60% or more, such as 75% or more, such as 90% or more, such as 95% or more and including 99% or more within 10 minutes or less of administration of the composition to the subject. In certain instances, the immediate release layer of nafamostat or pharmaceutically acceptable salt thereof is formulated to release all (i.e., 100%) of the nafamostat or pharmaceutically acceptable salt thereof within 10 minutes or less of administration of the composition to the subject. In certain instances, the immediate release layer of nafamostat or pharmaceutically acceptable salt thereof is formulated to release 50% or more of nafamostat or a pharmaceutically acceptable salt thereof immediately after administration of the composition to the subject, such as 60% or more, such as 75% or more, such as 90% or more, such as 95% or more and including 99% or more immediately after administration of the composition to the subject.

The amount of nafamostat or a pharmaceutically acceptable salt thereof present in the immediate release layer of each bead may be 0.000001 mg or more, such as 0.00001 mg or more, such as 0.0001 mg or more, such as 0.001 mg or more, such as 0.01 mg or more, such as 0.1 mg or more, such as 0.5 mg or more, such as 1 mg or more and including 2 mg or more. In some embodiments, the drug loading of nafamostat or pharmaceutically acceptable salt thereof in the immediate release layer of each bead is from 1% w/w to 25% w/w, such as from 2% w/w to 24% w/w, such as from 3% w/w to 23% w/w, such as from 4% w/w to 22% w/w, such as from 5% w/w to 21% w/w, such as from 6% w/w to 20% w/w, such as from 7% w/w to 19% w/w, such as from 8% w/w to 18% w/w, such as from 9% w/w to 15% w/w and including from 11% w/w to 13% w/w.

The composition of controlled release nafamostat or pharmaceutically acceptable salt thereof may be formulated in any convenient form suitable for oral (including buccal and sublingual) administration for example as a tablet, capsule, powder, suspension, dispersion or emulsion. In some embodiments, the controlled release nafamostat or pharmaceutically acceptable salt thereof is formulated for administration to the respiratory system of the subject, such as by pulmonary administration. For example, compositions described herein may be formulated for administration by inhalation (e.g., dry powder inhalation and aerosol inhalation), intratracheal instillation (delivery of into the airways by syringe), intratracheal delivery and insufflation (administration of powder formulation by syringe or any other similar device into the airways), nebulization. In some instances, compositions are formulated for dry powder inhalation or aerosol inhalation and may include a propellant such as hydrofluroalkanes, chlorofluocarbons, propane, nitrogen, or a mixture thereof. Aerosol formulations are stable dispersions or suspensions of solid material and liquid droplets in a gaseous medium and can be placed into pressurized acceptable propellants, such as hydrofluoroalkanes (HFAs, such as HFA-134a and HFA-227, or a mixture thereof), dichlorodifluoromethane (or other chlorofluorocarbon propellants such as a mixture of Propellants 11,12, and/or 114), propane, nitrogen, and the like.

The composition can contain components conventional in pharmaceutical preparations, e.g., one or more carriers, binders, lubricants, excipients (e.g., to impart controlled release characteristics), pH modifiers, sweeteners, bulking agents, coloring agents or further active agents. The pharmaceutical composition according to the embodiments can further comprise a pharmaceutically acceptable carrier.

The amount of nafamostat or a pharmaceutically acceptable salt thereof in a unit composition, for example, a capsule of the controlled release nafamostat or pharmaceutically acceptable salt thereof, may include from 1 mg and 500 mg of nafamostat or pharmaceutically acceptable salt thereof, for example, between: 1 and 10 mg, 10 and 20 mg, 20 and 30 mg, 30 and 40 mg, 40 and 50 mg, 50 and 60 mg, 60 and 70 mg, 70 and 80 mg, 80 and 90 mg, 90 and 100 mg, 100 and 110 mg, 110 and 120 mg, 120 and 130 mg, 130 and 140 mg, 140 and 150 mg, 150 and 160 mg, 160 and 170 mg, 170 and 180 mg, 180 and 190 mg, 190 and 200 mg, 200 and 210 mg, 210 and 220 mg, 220 and 230 mg, 230 and 240 mg, 240 and 250 mg, 250 and 260 mg, 260 and 270 mg, 270 and 280 mg, 280 and 290 mg, 290 and 300 mg, 300 and 310 mg, 310 and 320 mg, 320 and 330 mg, 330 and 340 mg, 340 and 350 mg, 350 and 360 mg, 360 and 370 mg, 370 and 380 mg, 380 and 390 mg, 390 and 400 mg, 400 and 410 mg, 410 and 420 mg, 420 and 430 mg, 430 and 440 mg, 440 and 450 mg, 450 and 460 mg, 460 and 470 mg, 470 and 480 mg, 480 and 490 mg and between 490 and 500 mg.

In certain embodiments, the controlled release compositions further includes an amount of immediate release nafamostat or pharmaceutically acceptable salt thereof, such as included within a capsule of the controlled release beads. In some instances, the immediate release nafamostat or pharmaceutically acceptable salt thereof is present in the composition (e.g., within the capsule) in form of a powder. In other instances, the immediate release nafamostat or pharmaceutically acceptable salt thereof is present in the composition (e.g., within the capsule) in form of a granulate. The amount of immediate release nafamostat or pharmaceutically acceptable salt thereof present in the composition may range from 1 mg to 200 mg, such as from 2 mg to 190 mg, such as from 3 mg to 180 mg, such as from 4 mg to 170 mg, such as from 5 mg to 160 mg, such as from 6 mg to 150 mg, such as from 7 mg to 140 mg, such as from 8 mg to 130 mg, such as from 9 mg to 120 mg and including from 10 mg to 100 mg.

Aspects of the present disclosure also include methods for administering the controlled release nafamostat or pharmaceutically acceptable salt thereof to a subject. In practicing the subject methods according to certain embodiments, one or more doses of the controlled release nafamostat composition is orally (including buccally or sublingually) administered to the subject. In certain instances, controlled release nafamostat compositions are administered to the respiratory system, such as by pulmonary administration. For example, compositions described herein may be administered according to certain embodiments by inhalation (e.g., dry powder inhalation and aerosol inhalation), intratracheal instillation (delivery of into the airways by syringe), intratracheal delivery and insufflation (administration of powder formulation by syringe or any other similar device into the airways), nebulization. In some instances, the administration is by dry powder inhalation or aerosol inhalation together with a propellant such as hydrofluroalkanes, chlorofluocarbons, propane, nitrogen, or a mixture thereof. Aerosol formulations are stable dispersions or suspensions of solid material and liquid droplets in a gaseous medium and can be placed into pressurized acceptable propellants, such as hydrofluoroalkanes (HFAs, such as HFA-134a and HFA-227, or a mixture thereof), dichlorodifluoromethane (or other chlorofluorocarbon propellants such as a mixture of Propellants 11,12, and/or 114), propane, nitrogen, and the like.

The dosage amount of the controlled release nafamostat composition administered to the subject may vary, ranging from about 0.01 mg/kg to 20 mg/kg per day, such as from 0.05 mg/kg to 19 mg/kg per day, such as 0.1 mg/kg to 18 mg/kg per day, such as 0.5 mg/kg to 17 mg/kg per day, such as 1 mg/kg to 16 mg/kg per day, and including 1 mg/kg to 15 mg/kg per day. In embodiments, the controlled release nafamostat composition may be administered to the subject once per day, twice per day, three times per day, four times per day, five times per day or at some other interval.

Each treatment interval with the controlled release nafamostat composition may be 1 day or longer, such as 2 days or longer, such as 3 days or longer, such as 4 days or longer, such as 5 days or longer, such as 6 days or longer, such as 7 days or longer, such as 2 weeks or longer, such as 3 weeks or longer, such as 4 weeks or longer, such as 8 weeks or longer, such as 12 weeks or longer, such as 16 weeks or longer, such as 20 weeks or longer, such as 24 weeks or longer, such as 28 weeks or longer, such as 32 weeks or longer, such as 36 weeks or longer, such as 40 weeks or longer, such as 44 weeks or longer, such as 48 weeks or longer and including 52 weeks or longer. In certain embodiments, protocols may include multiple dosage intervals. In practicing methods of the present disclosure, treatment regimens may include two or more dosage intervals, such as three or more dosage intervals, such as four or more dosage intervals, such as five or more dosage intervals, including ten or more dosage intervals.

The duration between dosage intervals in a multiple dosage interval treatment protocol may vary, depending on the physiology of the subject or by the treatment protocol as determined by a health care professional. For example, the duration between dosage intervals in a multiple dosage treatment protocol may be predetermined and follow at regular intervals. As such, the time between dosage intervals may vary and may be 1 day or longer, such as 2 days or longer, such as 4 days or longer, such as 6 days or longer, such as 8 days or longer, such as 12 days or longer, such as 16 days or longer and including 24 days or longer. In certain embodiments, multiple dosage interval protocols provide for a time between dosage intervals of 1 week or longer, such as 2 weeks or longer, such as 3 weeks or longer, such as 4 weeks or longer, such as weeks or longer, including 6 weeks or longer.

In certain embodiments, the controlled release nafamostat compositions described herein may be administered prior to, concurrent with, or subsequent to other therapeutic agents for treating the same or an unrelated condition. If provided at the same time as another therapeutic agent, the controlled release nafamostat composition may be administered in the same or in a different composition. Thus, the controlled release nafamostat composition and other therapeutic agents can be administered to the subject by way of concurrent therapy. By "concurrent therapy" is intended administration to a subject such that the therapeutic effect of the combination of the substances is caused in the subject undergoing therapy. Administration of the separate pharmaceutical compositions can be performed simultaneously or at different times (i.e., sequentially, in either order, on the same day, or on different days), so long as the therapeutic effect of the combination of these substances is caused in the subject undergoing therapy.

Aspects, including embodiments, of the subject matter described herein may be beneficial alone or in combination, with one or more other aspects or embodiments. Without limiting the description, certain non-limiting aspects of the disclosure numbered 1-40 are provided below. As will be apparent to those of skill in the art upon reading this disclosure, each of the individually numbered aspects may be used or combined with any of the preceding or following individually numbered aspects. This is intended to provide support for all such combinations of aspects and is 20 not limited to combinations of aspects explicitly provided below:

1. A composition comprising nafamostat or a pharmaceutically acceptable salt thereof, wherein the composition provides for controlled release of the nafamostat or pharmaceutically acceptable salt thereof to a subject for an extended period of time.
2. The composition of 1, wherein the composition comprises a plurality of controlled release beads, each bead comprising:

a core;

an active agent layer comprising nafamostat or a pharmaceutically acceptable salt thereof; and a controlled release layer comprising one or more polymers formulated in an amount sufficient to provide for controlled release of the nafamostat or pharmaceutically acceptable salt thereof.

3. The composition of 2, wherein the core comprises a cellulose polymer, or silicon dioxide, or a sugar selected from the group consisting of glucose, sucrose, lactose, mannitol, xylitol, and sorbitol.
4. The composition of 3, wherein the core comprises microcrystalline cellulose (MCC).
5. The composition of any one of 1-4, wherein the active agent layer further comprises a binder.
6. The composition of any one of 1-4, wherein the binder comprises hydroxypropyl methylcellulose.
7. The composition of any one of 1-6, wherein the controlled release layer comprises an acrylate copolymer.
8. The composition of 7, wherein the acrylate copolymer comprises poly(ethylacrylate, methyl-methacrylate and chlorotrimethyl-ammonioethyl methacrylate).
9. The composition of 8, wherein the acrylate copolymer comprises poly(ethylacrylate, methyl-methacrylate and chlorotrimethyl-ammonioethyl methacrylate) containing quaternary ammonium groups.
10. The composition of 9, wherein the acrylate copolymer comprises a combination of:

acrylate copolymer A comprising poly(ethylacrylate, methyl-methacrylate and chlorotrimethyl-ammonioethyl methacrylate) comprising about 50 mEq of quaternary ammonium groups per 100 g of polymer; and acrylate copolymer B comprising poly(ethylacrylate, methyl-methacrylate and chlorotrimethyl-ammonioethyl methacrylate) comprising about 25 mEq of quaternary ammonium groups per 100 g of polymer.

11. The composition of 10, wherein the acrylate copolymer comprises 20% by weight acrylate copolymer B and 80% by weight acrylate copolymer A.
12. The composition of 10, wherein the acrylate copolymer comprises 50% by weight acrylate copolymer B and 50% by weight acrylate copolymer A.
13. The composition of 10, wherein the acrylate copolymer comprises 80% by weight acrylate copolymer B and 20% by weight acrylate copolymer A.
14. The composition of 10, wherein the acrylate copolymer comprises 100% by weight acrylate copolymer A.
15. The composition of 10, wherein the acrylate copolymer comprises 100% by weight acrylate copolymer B.
16. The composition of 10, wherein the acrylate copolymer comprises 95% by weight acrylate copolymer B and 5% by weight acrylate copolymer A.
17. The composition of 10, wherein the acrylate copolymer comprises 93% by weight acrylate copolymer B and 7% by weight acrylate copolymer A.
18. The composition of 10, wherein the acrylate copolymer comprises 92% by weight acrylate copolymer B and 8% by weight acrylate copolymer A.
19. The composition of 10, wherein the acrylate copolymer comprises 90% by weight acrylate copolymer B and 10% by weight acrylate copolymer A.
20. The composition of 10, wherein the acrylate copolymer comprises 87% by weight acrylate copolymer B and 13% by weight acrylate copolymer A.
21. The composition of any of 7 to 20, wherein the acrylate copolymer comprises from 5% and 30% by weight of each of the plurality of beads.
22. The composition of any of 2 to 21, wherein one or more of the active agent layer and the controlled release layer further comprise magnesium silicate.
23. The composition of any of 2 to 22, wherein one or more of the active agent layer and the controlled release layer further comprise a plasticizer.
24. The composition of 23, wherein the plasticizer is triethyl citrate.
25. The composition of any of 2 to 24, wherein each of the plurality of beads comprises from 5% and 20% by weight of the nafamostat or a pharmaceutically acceptable salt thereof.
26. The composition of 25, wherein each of the plurality of beads comprises from 10% to 15% by weight of the nafamostat or a pharmaceutically acceptable salt thereof.
27. The composition of 25, wherein each of the plurality of beads comprises from 11% to 12% by weight of the nafamostat or a pharmaceutically acceptable salt thereof.
28. The composition according to any one of 1-27, wherein the plurality of beads are configured to release 50% or more of the nafamostat or pharmaceutically acceptable salt thereof within 6 hours after administration.
29. The composition according to any one of 1-27, wherein the plurality of beads are configured to release 75% or more of the nafamostat or pharmaceutically acceptable salt thereof within 6 hours after administration.
30. The composition according to any one of 1-27, wherein the plurality of beads are configured to release 90% or more of the nafamostat or pharmaceutically acceptable salt thereof within 6 hours after administration.
31. The composition according to any one of 1-27, wherein the plurality of beads are configured to provide for release of nafamostat or pharmaceutically acceptable salt thereof at a first rate for a first predetermined period of time followed by release of the nafamostat or pharmaceutically acceptable salt thereof at a second rate for a second predetermined period of time.
32. The composition of any of 1 to 31, further comprising nafamostat or a pharmaceutically acceptable salt thereof in an immediate release form that provides for an immediate release of nafamostat or pharmaceutically acceptable salt thereof to the subject.
33. The composition of 32, wherein the nafamostat or a pharmaceutically acceptable salt thereof in the immediate release form comprises nafamostat or a pharmaceutically acceptable salt thereof in a powder form.

34. The composition of 32, wherein nafamostat or a pharmaceutically acceptable salt thereof in the immediate release form comprises a layer of nafamostat or a pharmaceutically acceptable salt thereof positioned over the controlled release layer of the plurality of the controlled release beads.
35. The composition of 32, wherein nafamostat or a pharmaceutically acceptable salt thereof in the immediate release form comprises a plurality of immediate release beads.
36. A method comprising orally administering to a subject in need thereof a composition of any one of 1-35.
37. A method comprising administering to the respiratory system of a subject in need thereof a composition of any one of 1-35.
38. The method of 37, wherein the composition is administered by inhalation, intratracheal instillation, intratracheal delivery, insufflation, nebulization or a combination thereof.
39. The method according to any one of 37-38, wherein the composition further comprises a propellant.
40. The method according to 39, wherein the propellant comprises hydrofluroalkanes, chlorofluocarbons, propane, nitrogen, or a mixture thereof.

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used.

The oxycodone-derivative used in the present experiments is referred to herein as KC-8 (N-1-[3-(oxycodone-6-enol-carbonyl-methyl-amino)-2,2-dimethyl-propylamine]-arginine-glycine-malonic acid) and has the structure shown below. The left side of the molecule is the oxycodone group. Moving to the right is a linker with structure-C(O) $N(CH_3)CH_2C(CH_3)_2CH_2$-followed by a peptide of the formula Arg-Gly-Mal.

(KC-8)

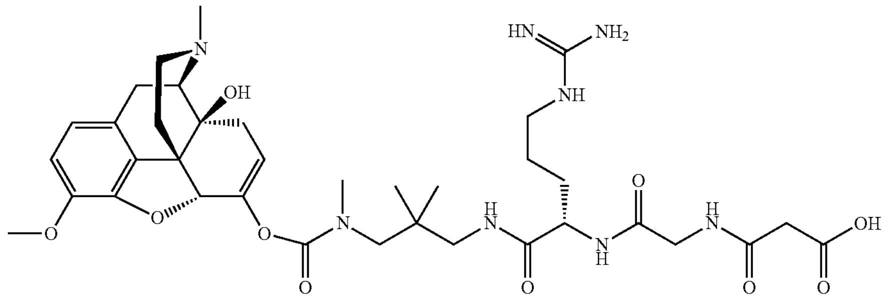

FIG. 1 shows how KC-8 can be activated by the digestive system. First, the N—C bond between the linker and the peptide group is cleaved or bioactivated by the digestive enzyme trypsin. As such, KC-8 can be referred to as trypsin activated. Next, after the terminal amine group of the linker has been separated from the peptide protecting group, the linker undergoes an intramolecular cyclization, thereby releasing a cyclic urea byproduct. As a result, the oxycodone molecule is formed, which can then cause pharmacological effects such as pain inhibition. As such, generation of the active oxycodone drug can be caused by cleavage of the N—C bond by trypsin, which is an enzyme located in the digestive tract.

Example 1-Effect of Nafamostat on Pharmacokinetics of KC-8 in Rats

The drug nafamostat mesylate was added to the formulations containing the KC-8 oxycodone-derivative. In the examples described herein, the terms "nafamostat mesylate" and "nafamostat" are used interchangeably.

Formulations containing both KC-8 and optionally nafamostat were administered orally to rats. The KC-8 dose was 5 mg/kg and the nafamostat concentration was 0, 0.1, 0.5, or 1 mg/kg. Plasma concentrations of active oxycodone were measured at various time intervals over 24 hours after administration.

Figure 2:
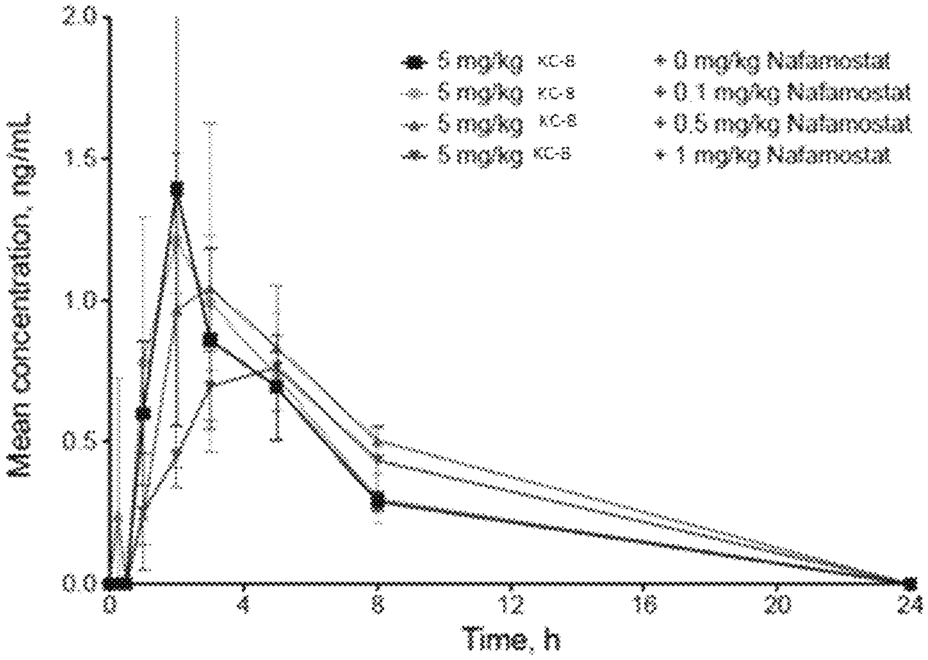
FIG. 2 shows the mean blood concentration of oxycodone in rats that were orally administered 5 mg/kg of the oxycodone derivative KC-8 with either 0, 0.1, 0.5, or 1 mg/kg of nafamostat over time.

As shown in FIG. 2, with 0 or 0.1 mg/kg of nafamostat the oxycodone concentration spiked at about 2 hours with a concentration of about 1.3 or 1.4 ng/ml. In contrast, additional nafamostat reduced the maximum oxycodone concentration to a peak of about 0.75 ng/ml at about 5 hours. The error bars represent one standard deviation.

Figure 3:
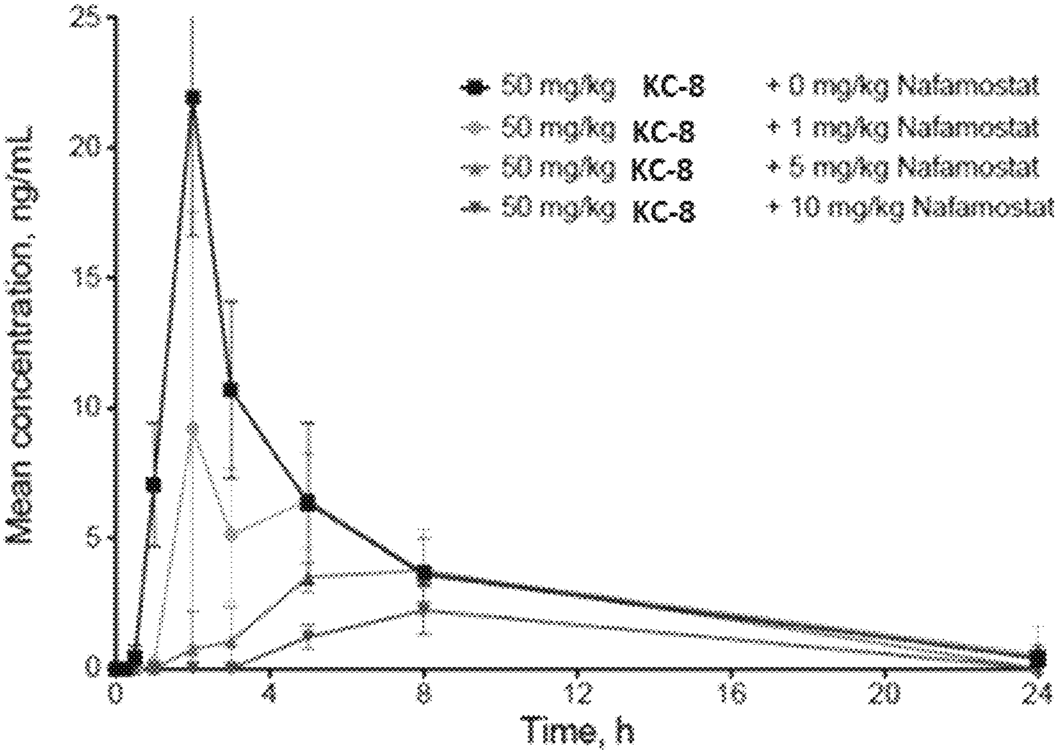
FIG. 3 shows the mean blood concentration of oxycodone in rats that were orally administered 50 mg/kg of the oxycodone derivative KC-8 with either 0, 1, 5, or 10 mg/kg of nafamostat over time.

As shown in FIG. 3, rats were administered higher concentrations of both KC-8 and nafamostat that are approximately equal to the dose a human would receive if ingesting 10 pills of KC-8. In particular, the rats received 50 mg/kg of KC-8 and 0, 1, 5, or 10 mg/kg of nafamostat. With zero nafamostat, blood plasma concentration experienced a maximum of about 22 ng/ml at about 2 hours, wherein the concentration rapidly descended thereafter. In alignment with the data of FIG. 2, higher concentrations of nafamostat reduced the peak concentration to about 3 ng/ml at about 8 hours.

Figure 4:
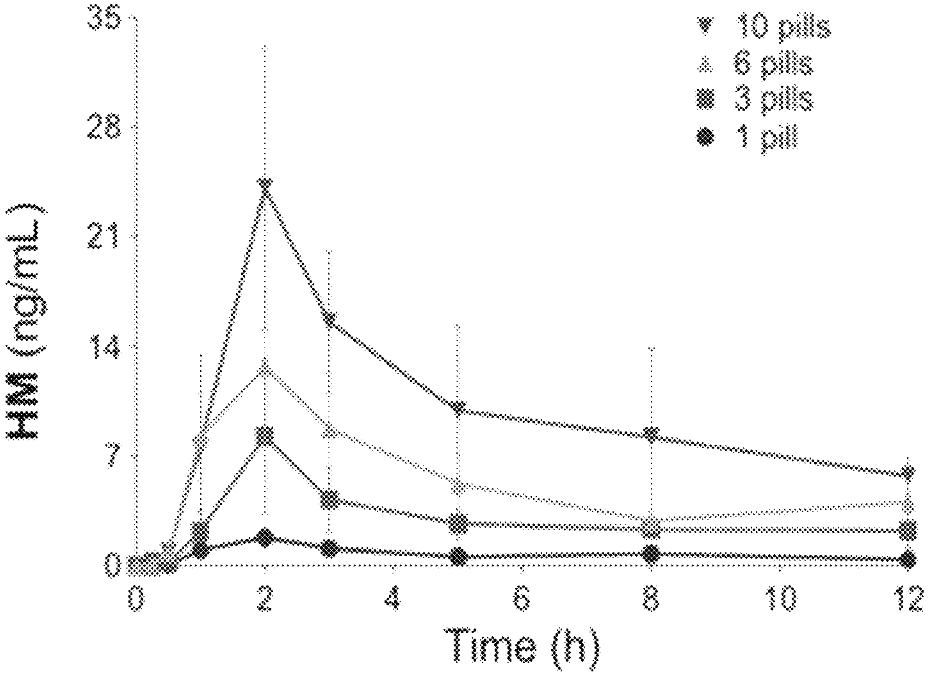
FIG. 4 shows the mean blood, concentration of hydromorphone in rats that were orally administered 1, 3, 6, or 10 pills of a hydromorphone derivative but no nafamostat.
Figure 5:
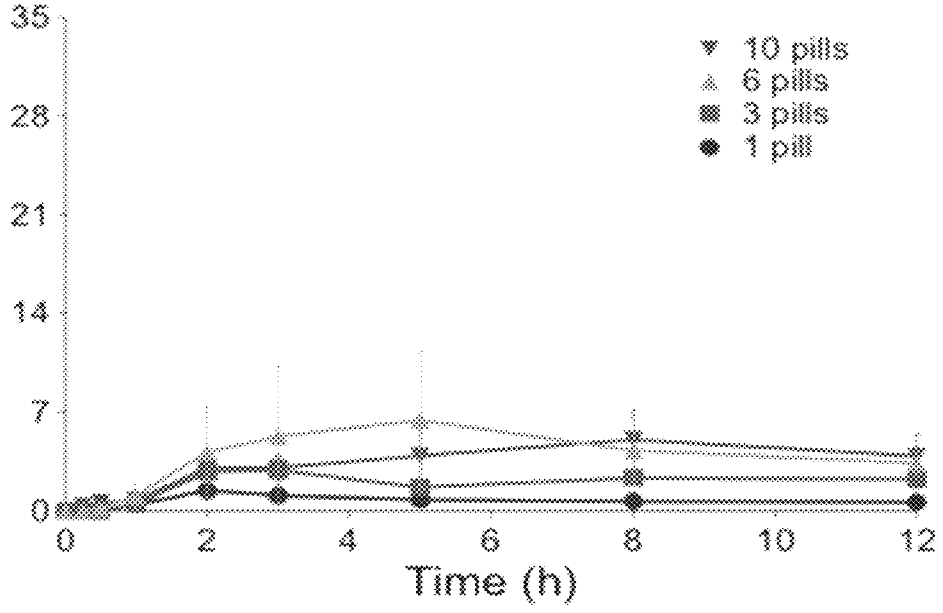
FIG. 5 shows the mean blood concentration of hydromorphone in rats that were orally administered 1, 3, 6, or 10 pills of a hydromorphone derivative that also contained nafamostat.

The rat experiments were repeated with a derivative of hydromorphone (referred to herein as PF329), which is another known pain medication. FIGS. 4 and 5 show the blood concentration of active hydromorphone (HM) after the administration of 1, 3, 6, or 10 pills, either without or with nafamostat. In other words, the FIG. 5 pills contained nafamostat whereas the FIG. 4 pills did not. The figures show that administering more pills in FIG. 4 resulted in a significant increase in hydromorphone concentration, but in FIG. 5 there was little increase due to the moderating effects of nafamostat.

Thus, Experiment 1 showed that co-administering nafamostat with an oxycodone or hydromorphone derivative significantly reduced the maximum concentration of active drug in blood plasma and also resulted in a more stable concentration of the active drug over time.

Example 2: Effect of Nafamostat on Pharmacokinetics of KC-8 in Humans

Figure 6:
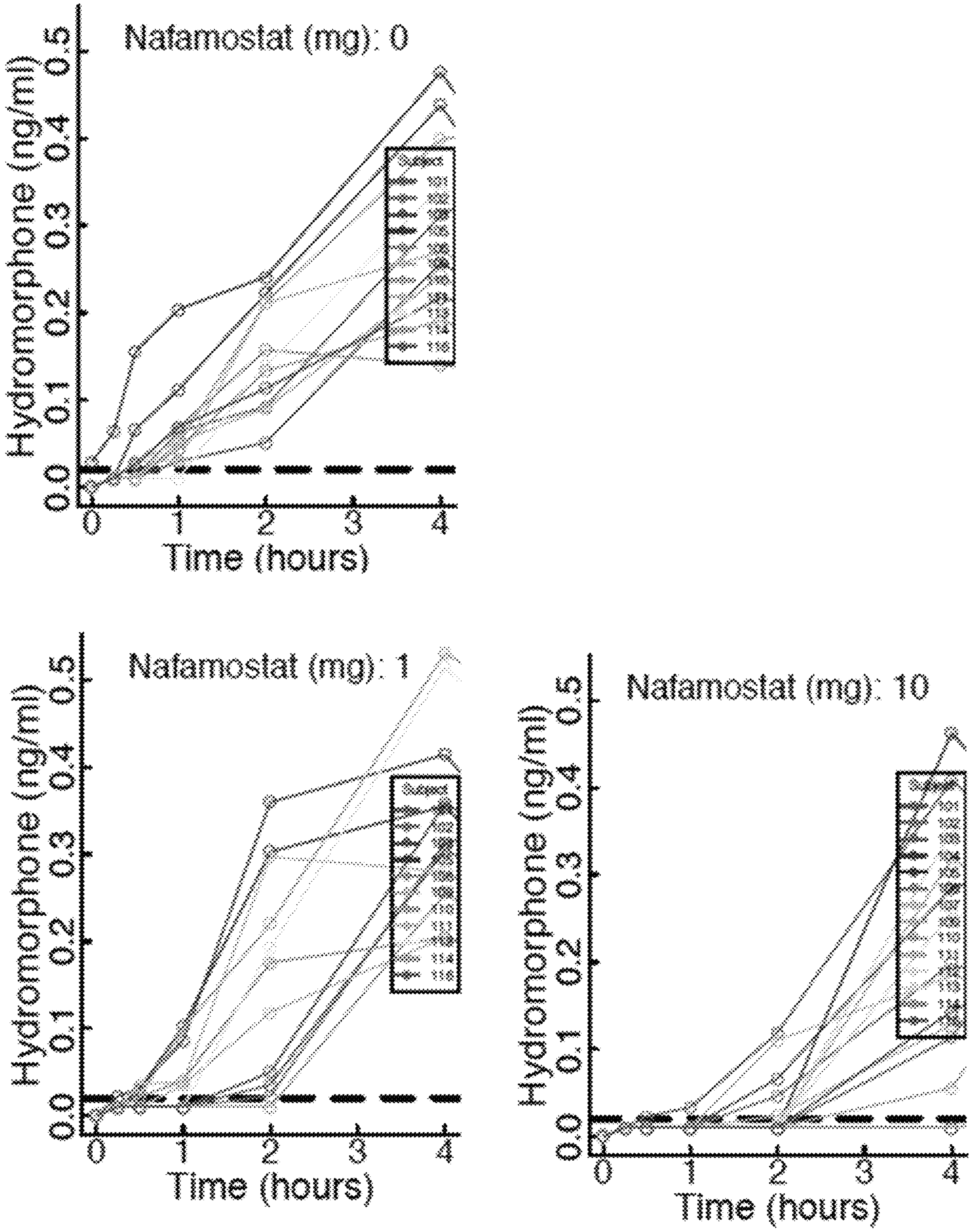
FIG. 6 shows the blood concentration of multiple human patients of hydromorphone after being administered a hydromorphone derivative and 0, 1, or 10 mg of nafamostat.

Whereas the Example 1 experiments tested the effect of nafamostat in rats, Experiment 2 measured the effect when administered to humans. The pharmacokinetics in humans appeared to be different than in rats. As shown in FIG. 6, the hydromorphone derivative of PF329 was administered with 0, 1, or 10 mg of nafamostat. With 0 mg of nafamostat, the blood concentration of hydromorphone increased starting at 0 hours and reaching about 0.4 ng/ml. With 1 or 10 mg of nafamostat, the increase was delayed until 1 or 2 hours, but the peak concentration appeared to also reach about 0.4 ng/ml. Thus, it appeared that the effect of nafamostat in humans was different than in rats.

Example 3: Preparation of Immediate Release Nafamostat Composition

Nafamostat compositions containing immediate release beads were prepared. Each immediate release bead includes a microcrystalline cellulose core and an active agent layer of nafamostat mesylate.

A coating solution of nafamostat mesylate was prepared by adding methocel to water and leaving to stir at 250 rpm for 25 minutes. 29 g of nafamostat mesylate was slowly added and stirred for a further 5 minutes until fully dissolved. This produced a 5 wt % nafamostat mesylate solution. The remaining nafamostat mesylate was then added over another 10 minutes and mixed for another 10 minutes to yield a white uniform suspension. The suspension was left stirring overnight. The coating solution was placed onto a top pan balance and an overhead stirrer was set up to ensure the solution remained fully dispersed throughout the coating process. The components of the immediate release Nafamostat coating composition is summarized in Table 3.

Table 3. Immediate release Nafamostat mesylate coating solution

TABLE 3

Immediate release Nafamostat mesylate coating solution

| Component | % w/w | Quantity per 1000 g batch (g) |
|---|---|---|
| Nafamostat mesylate | 13.64<br>(8.80)[1] | 150.00<br>(96.80)[1] |
| Methocel E5 | 0.45 | 5.00 |
| Water for irrigation* | 85.91 | 945.00[2] |
| Total solution | 100.0000 | 1100.00 |

*Removed during the process
[1]Amount of free drug based on salt correction of 1.55
[2]incorrect amount of water used, 14.09% solids content instead of 15.5%

700 g of MCC CP-305 spheres were weighed out and loaded into the vessel and coating commenced. The pump speed was gradually increased from 1 g/min every 10-20 minutes until a maximum spray rate was achieved. A blow back cycle was not required. Coating was carried out for a total of 4.75 hours without any significant twinning or clumping being observed. The beads were cured for 30 minutes prior to collection. The processing parameters are presented in Table 4. The beads were collected passed through a 600 μm sieve, 698 g acceptable individual beads were collected, while 72 g twinned beads were collected.

TABLE 4

Coating parameters for Immediate release Nafamostat mesylate coating solutions

| | Set point | |
|---|---|---|
| Parameter | Batch 1 | Batch 2 |
| Drying air speed ($m^3\ min^{-1}$) | 0.20-0.45 | 0.20-0.35 |
| Air inlet temperature (° C.) | 71.9 (61.8-84.6) | 72.3 (63.0-78.0) |
| Product temperature (° C.) | 48.9 (47.5-51.4) | 47.5 (45.7-49.0) |
| Nozzle pressure (bar) | 0.75 (0.42-1.24) | 0.94 (0.47-1.00) |
| Nozzle flow rate ($L\ min^{-1}$) | 4.9 (2.9-5.5) | 5.3 (3.4-5.5) |
| Pump flow rate ($g\ min^{-1}$) | 0.44-2.96 | 086-2.67 |

The beads were collected and passed through a 600 μm sieve, 698 g individual beads were collected, while 72 g were twinned. In total 702 g coating solution was sprayed, a theoretical free drug loading of 7.99% w/w was achieved. Beads were tested for LOD, Assay, related substance and water content. The beads showed good uniformity indicating that an even coating had been achieved.

Example 4: Preparation of Active Agent Layer of Controlled Release Nafamostat Compositions The active agent layer of the Nafamostat controlled release beads were prepared. Each bead was prepared from a microcrystalline cellulose core and a coating layer of nafamostat mesylate. The composition of the coating solution is shown in Table 5.

TABLE 5

Active agent layer of Nafamostat controlled release beads coating solution

| Component | % w/w | Quantity per 1000 g batch (g) |
|---|---|---|
| Nafamostat mesylate | 13.64<br>(8.80)[1] | 150.00<br>(96.80)[1] |
| Methocel E5 | 0.45 | 5.00 |
| Water for irrigation* | 85.91 | 945.00[2] |
| Total solution | 100.0000 | 1100.00 |

*Removed during the process
[1]Amount of free drug based on salt correction of 1.55
[2]incorrect amount of water used, 14.09% solids content instead of 15.5%

The coating solution of nafamostat mesylate was prepared as described above for the immediate release nafamostat bead compositions and was left stirring overnight. 650 grams of microcrystalline cellulose CP-305 spheres were weighed out and loaded into the vessel and coating commenced. The pump speed was maintained at 1 g/min for 15 minutes before it was increased to 1.5 g/min. The pump speed was gradually increased to 3.0 g/min over the next hour based on observations made. During this time the nozzle pressure was gradually increased in line with the pump speed to maintain a good spray pattern. In total the process ran for 4.5 hours without any blockages or the need for the blowback feature. The beads were cured in the fluid bed vessel at 40° C. for 30 minutes, coating parameters are as presented in Table 4.

The beads were collected and passed through a 600 μm sieve, 532 g individual beads were collected, while 194 g were twinned. In total 655 g coating solution was sprayed, a theoretical free drug loading of 8.40% w/w was achieved. Beads were tested for LOD, Assay, related substance and water content.

Example 6: Preparation of Controlled Release Nafamostat Compositions

Nafamostat compositions containing controlled release beads were prepared. Each controlled release bead includes a microcrystalline cellulose core and an active agent layer of nafamostat mesylate and a controlled release polymeric coating layer. The active agent layer of nafamostat mesylate was prepared as set forth in Example 4. A polymeric controlled release coating solution with an 87:13 ratio of Eudragit RS: Eudragit RL was prepared as summarized in Table 6. In another embodiment, the proportion of talc in the solution was halved relative to the other components as shown in Table 7.

TABLE 6

Controlled release polymer layer of Nafamostat controlled release beads coating solution (87:13 Eudragit RS:Eudragit RL)

| Component | % w/w | Quantity per 300 g batch (g)[1] |
|---|---|---|
| Eudragit RS PO | 3.2625 | 27.1875 |
| Eudragit RL PO | 0.4875 | 4.0625 |
| Triethyl Citrate | 0.3750 | 3.1250 |
| Micronized Talc | 1.8750 | 15.6250 |
| Acetone*,2 | 35.8140 | 298.4500 |
| Isopropanol, Anhydrous*,2 | 53.7022 | 447.5183 |
| Water for irrigation*,2 | 4.4838 | 37.3650 |
| Total solution | 100.0000 | 833.3330 |
| Nafamostat Intermediate IR Beads | | 250.0000 |

*Removed during the process
[1]drug layering solution 6% solids
[2]Acetone/Isopropanol/water = 38.10:57.13:4.77 ratio

TABLE 7

Controlled release polymer layer of Nafamostat controlled release beads coating solution (87:13 Eudragit RS:Eudragit RL)

| Component | % w/w | Quantity per batch (g)[1] |
|---|---|---|
| Eudragit RS PO | 6.266 | 54.37 |
| Eudragit RL PO | 0.937 | 8.13 |
| Triethyl Citrate | 0.72 | 6.25 |
| Micronized Talc | 1.8 | 15.62 |
| Acetone*,2 | 34.395 | 298.45 |
| Isopropanol, Anhydrous*,2 | 51.575 | 447.52 |
| Water for irrigation*,2 | 4.307 | 37.37 |
| Total solution | 100.000 | 867.71 |

*Removed during the process
[1]ER coating suspension 9.72% solids
[2]Acetone/Isopropanol/water = 38.10:57.13:4.77 ratio A Procept Fluid Bed was set up, using the 1 L vessel, 0.4 mm nozzle and no wurster column. 250 g of active agent layer containing beads (microcrystalline cellulose coated with nafamostat mesylate prepared as described above) were weighed out and loaded into the vessel. The coating solution was prepared producing a white opaque solution that was uniformly dispersed. The coating solution was placed onto a top pan balance and an overhead stirrer was set up at 250 rpm to ensure the solution remained fully dispersed throughout the coating process. The coating solution was primed into the line and gun to check for leaks/air bubbles.

Coating was started at an initial spray rate of 0.5 g/min, this was gradually increased throughout the duration of the coating process until a maximum of 2.5 g/min was achieved. Significant static issues were observed, with lots of beads sticking to the inside of the vessel and onto the filters. A static gun had to be used almost constantly to ensure the beads did not build up and stop flowing. After 2.5 hours the process was stopped as clumps of beads had started to form. It was noted that the talc had sedimented in the line, possibly contributing to the clumping of the beads. Approximately 207 g coating solution was sprayed resulting in a coating weight gain of 4.73%. Using a 600 μm sieve, the ER coated beads were screened for twins.

Figure 12:
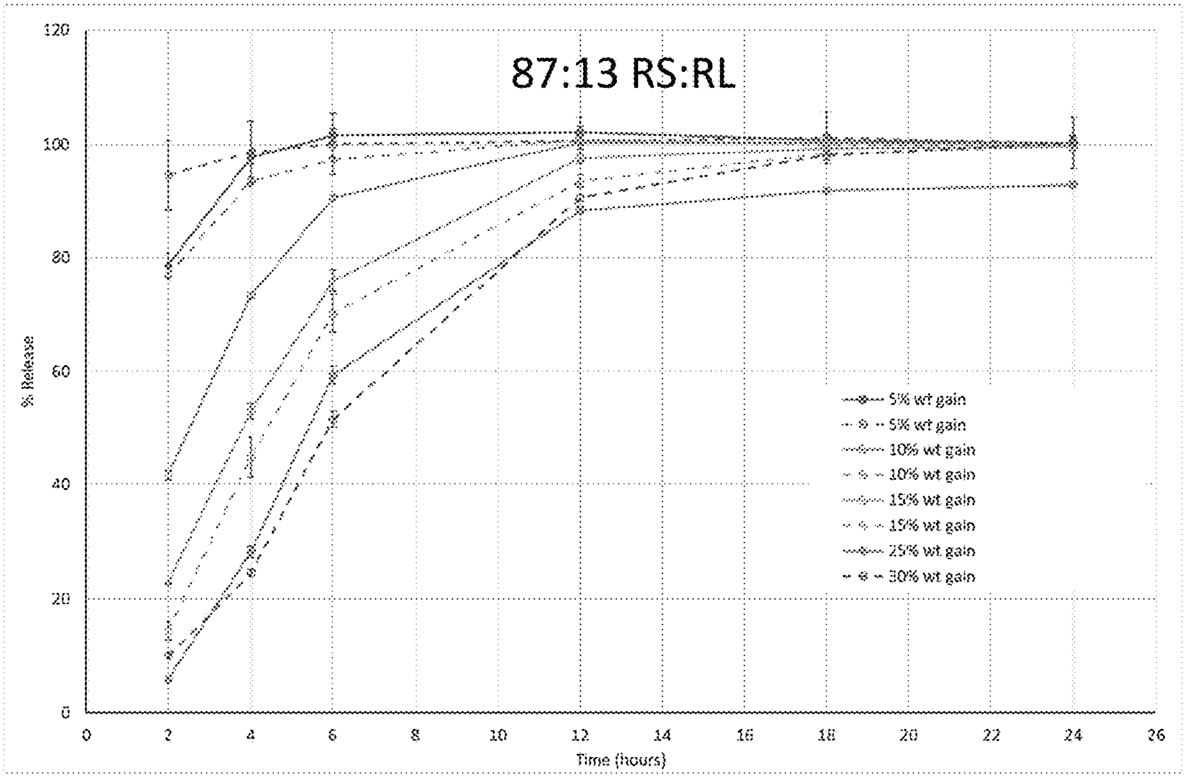
FIG. 12 shows a comparison of release profiles of nafamostat from the controlled release beads having an 87:13 (Eudragit RS: Eudragit RL) ratio with increasing weight gain.

FIG. 12 depicts a comparison of release profiles of nafamostat from the controlled release beads having an 87:13 (Eudragit RS: Eudragit RL) ratio with increasing weight gain.

Example 7: Preparation of Controlled Release Nafamostat Compositions

Nafamostat compositions containing controlled release beads were prepared. Each controlled release bead includes a microcrystalline cellulose core and an active agent layer of nafamostat mesylate and a controlled release polymeric coating layer. The active agent layer of nafamostat mesylate was prepared as set forth in Example 4. A polymeric controlled release coating solution with a 90:10 ratio of Eudragit RS: Eudragit RL was prepared as summarized in Table 8.

TABLE 8

Controlled release polymer layer of Nafamostat controlled release beads coating solution (90:10 Eudragit RS:Eudragit RL)

| Component | % w/w | Quantity (g)[1] |
|---|---|---|
| Eudragit RS PO | 6.483 | 64.83 |
| Eudragit RL PO | 0.720 | 7.20 |
| Triethyl Citrate | 0.720 | 7.20 |
| Micronized Talc | 1.800 | 18.00 |
| Acetone*2 | 34.396 | 343.95 |
| Isopropanol, Anhydrous*,2 | 51.576 | 515.75 |
| Water for irrigation*,2 | 4.306 | 43.06 |
| Total solution | 100.0000 | 999.99 |

*Removed during the process
[1]ER coating solution 9.72% solids
[2]Acetone/Isopropanol/water = 38.10:57.13:4.77 ratio In order to produce controlled release beads with slower release rates, the ratio of Eudragit RS: Eudragit RL was changed to 90:10. The Procept Fluid Bed was set up as previously described and 250 g of nafamostat active agent layer containing beads (as described above) were weighed out and loaded into the vessel. The coating solution was prepared producing a white opaque solution that was uniformly dispersed.

Coating was started and remained at 2.0 g/min for the duration of the coating process. Static issues were observed, with lots of beads sticking to the inside of the vessel and onto the filters. The filter pressure rapidly increased in this coating run, reaching 50 mbar in only 30 minutes. The blowback feature on the fluid bed was tested, but it didn't make any significant difference to the filter pressure. The air speed, nozzle flow and nozzle pressure were therefore reduced and tightly controlled to enable the process to continue for longer.

The process ran for approximately 4 hours and 30 minutes, achieving a theoretical 20% weight gain. Samples of the beads were taken at 5%, 10% and 20%. The bulk beads were cured in the vessel for 30 minutes at 40° C. and the samples placed in the oven at 40° C. for overnight curing.

Figure 13:
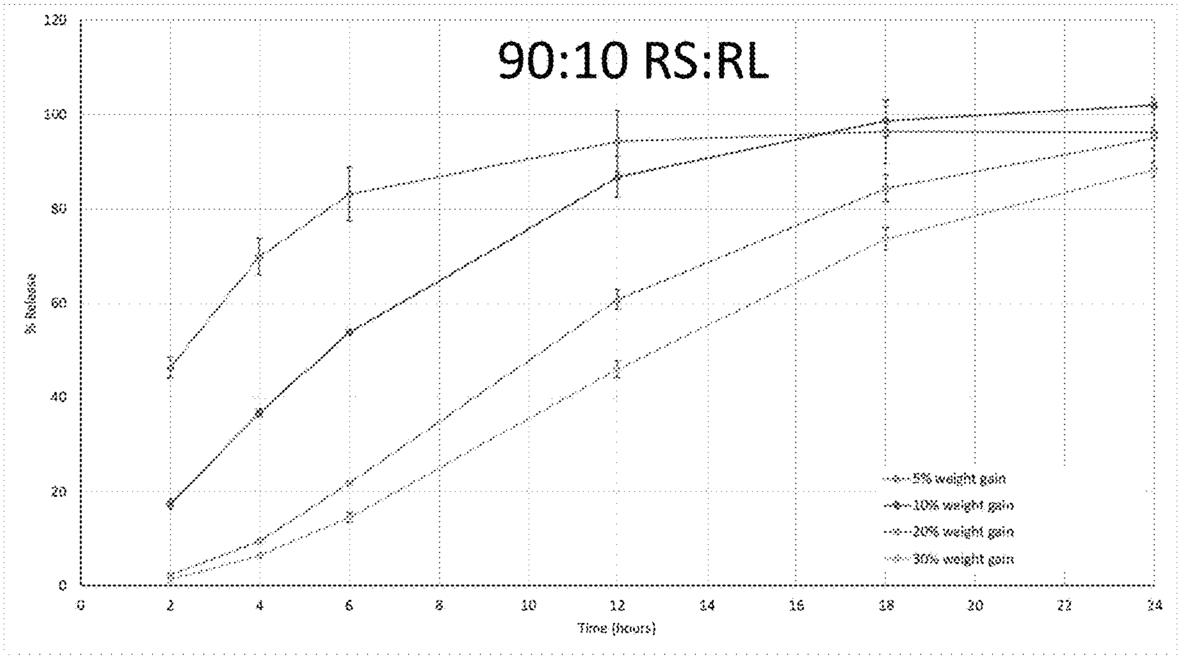
FIG. 13 shows a comparison of release profiles of nafamostat from the controlled release beads having a 90:10 (Eudragit RS: Eudragit RL) ratio with increasing weight gain.

The next morning the process was restarted, with the same bulk beads in the vessel and same coating solution. The filters were changed as they had exceeded 75 mbar. The aim of this additional coating was to try and achieve a 30% weight gain (an additional 10% on top of the 20% previously achieved). The process ran for a further 2 hours, a sample of the beads was taken at 30% weight gain and placed in the oven. Approximately 772 g coating solution was sprayed resulting in a theoretical coating weight gain of 30%. Using a 600 μm sieve, the ER coated beads were screened for twins. All weight gain samples were taken and analysed for dissolution and LOD. FIG. 13 shows a comparison of release profiles of nafamostat from the controlled release beads having a 90:10 (Eudragit RS: Eudragit RL) ratio with increasing weight gain.

Example 8: Preparation of Controlled Release Nafamostat Compositions

Nafamostat compositions containing controlled release beads were prepared. Each controlled release bead includes a microcrystalline cellulose core and an active agent layer of nafamostat mesylate and a controlled release polymeric coating layer. The active agent layer of nafamostat mesylate was prepared as set forth in Example 4. A polymeric controlled release coating solution with a 80:20 ratio of Eudragit RS: Eudragit RL was prepared as summarized in Table 9.

TABLE 9

Controlled release polymer layer of Nafamostat controlled release beads coating solution (80:20 Eudragit RS:Eudragit RL)

| Component | % w/w | Quantity (g)[1] |
|---|---|---|
| Eudragit RS PO | 5.762 | 28.81 |
| Eudragit RL PO | 1.440 | 7.20 |
| Triethyl Citrate | 0.720 | 3.60 |
| Micronized Talc | 1.800 | 9.00 |
| Acetone*,[2] | 34.396 | 171.98 |
| Isopropanol, Anhydrous*,[2] | 51.576 | 257.88 |
| Water for irrigation*,[2] | 4.306 | 21.53 |
| Total solution | 100.000 | 500.00 |

*Removed during the process
[1]ER coating suspension 9.72% solids
[2]Acetone/Isopropanol/water = 38.10:57.13:4.77 ratio In order to produce controlled release beads with faster release rates, the ratio of Eudragit RS: Eudragit RL was changed to 80:20. The Procept Fluid Bed was set up as previously described and 250 g of nafamostat active agent layer containing beads (as describeda above) were weighed out and loaded into the vessel. The coating solution was prepared producing a white opaque solution that was uniformly dispersed. Static in this trial was noticeable but could be controlled with the use of static guns. Stalactites formed on the bottom of the filters, but would disperse themselves. Avoiding touching the glass vessel helped to reduce the build-up of beads on the glass.

The process ran for approximately 3 hours, achieving a 15% weight gain. Samples of the beads were taken at 5% and 10%. The bulk beads were cured in the vessel and then transferred into a metal tray and placed into the oven overnight, along with the sample beads, at 40° C. By controlling the nozzle pressure and flow carefully, the filters didn't exceed 40 mbar allowing the process to continue running smoothly. Approximately 369 g coating solution was sprayed resulting in a theoretical coating weight gain of 15%. Using a 600 μm sieve, the ER coated beads were screened for twins.

Figure 14A:
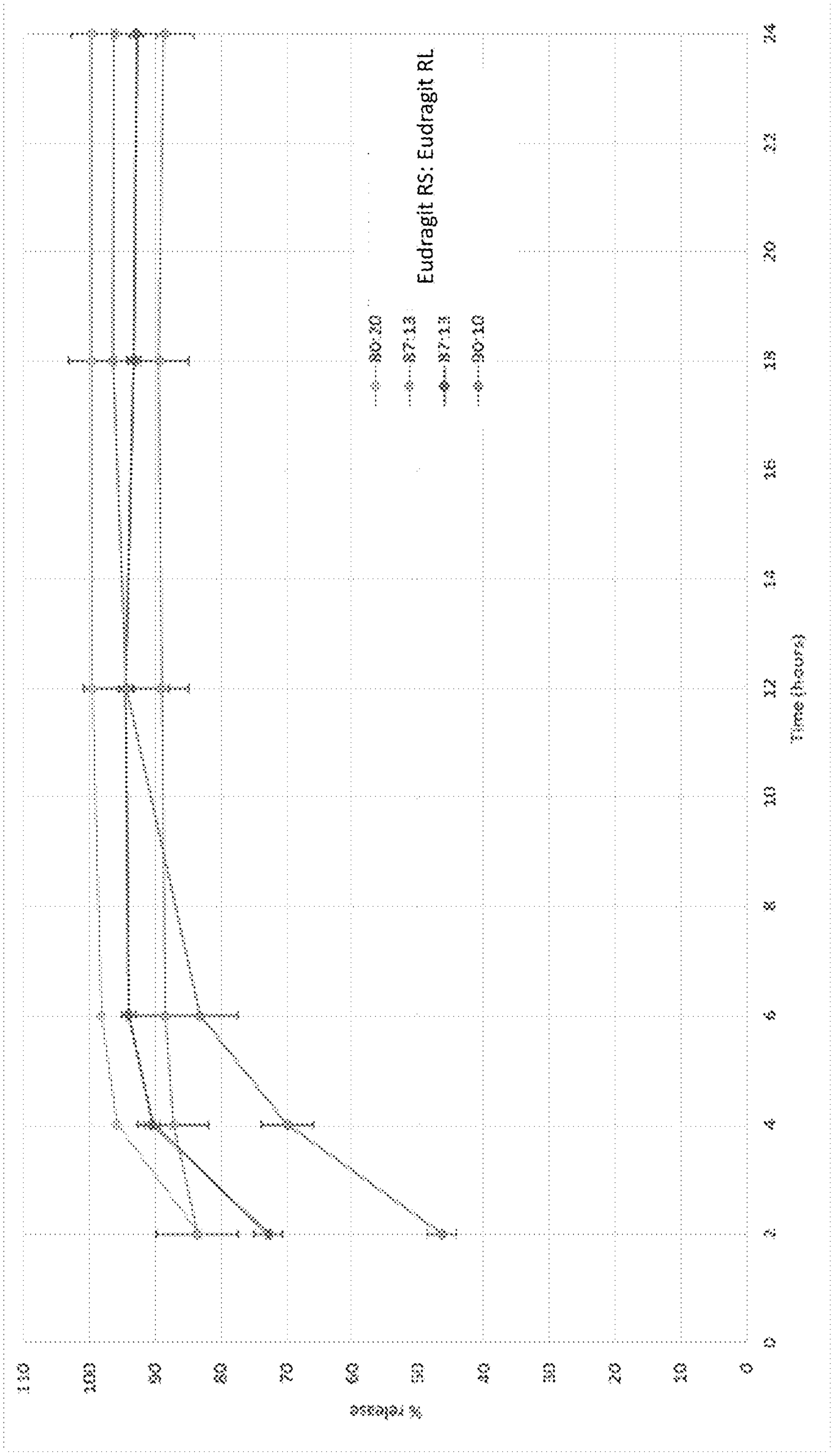
FIG. 14A shows a comparison of mean release profiles of nafamostat from the controlled release beads at 5% weight gain with different ratios of Eudragit RS: Eudragit RL in the controlled release polymeric layer.
Figure 14B:
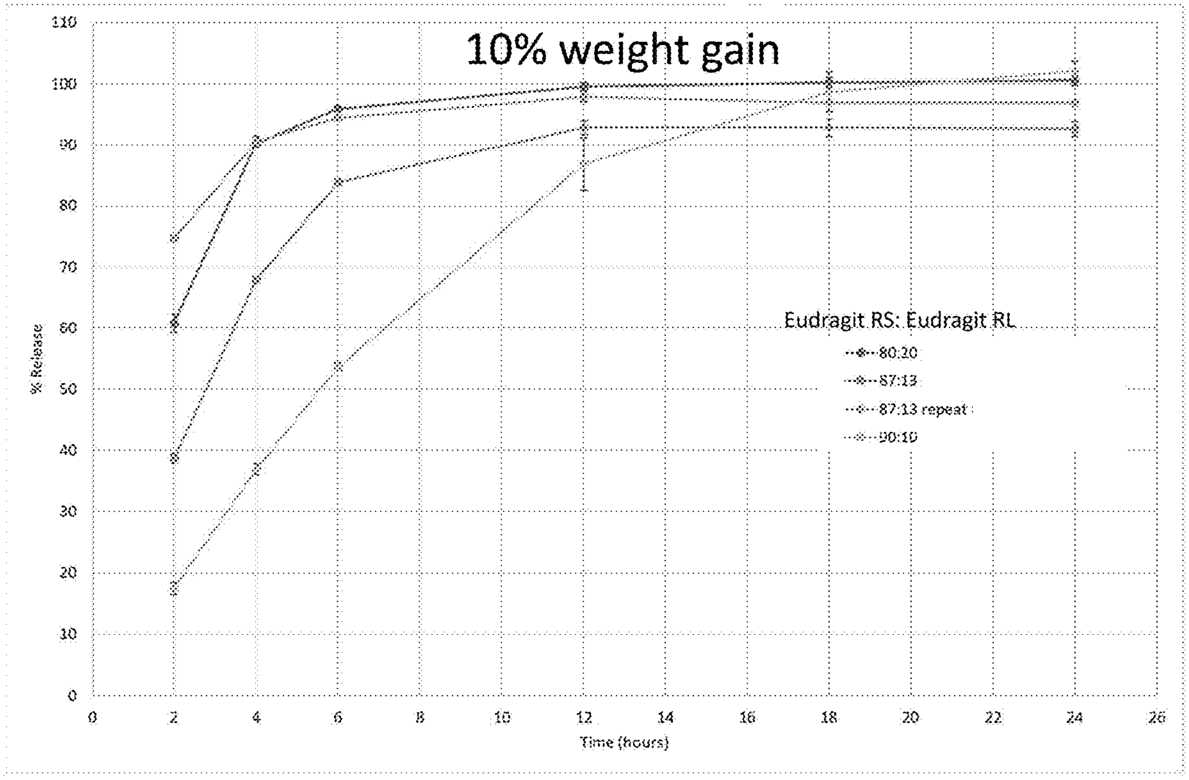
FIG. 14B shows a comparison of mean release profiles of nafamostat from the controlled release beads at 10% weight gain with different ratios of Eudragit RS: Eudragit RL in the controlled release polymeric layer.

A comparison of the mean release profiles of nafamostat for coated beads at 5% weight gain with different ratios of Eudragit RS: Eudragit RL is shown in FIG. 14A. A comparison of the mean release profiles of nafamostat for coated beads at 10% weight gain with different ratios of Eudragit RS: Eudragit RL is shown in FIG. 14B.

Example 9: Preparation of Controlled Release Nafamostat Compositions

Nafamostat compositions containing controlled release beads were prepared. Each controlled release bead includes a microcrystalline cellulose core and an active agent layer of nafamostat mesylate and a controlled release polymeric coating layer. The active agent layer of nafamostat mesylate was prepared as set forth in Example 4. A polymeric controlled release coating solution with a 92:8 ratio of Eudragit RS: Eudragit RL was prepared as summarized in Table 10. Syloid 244FP was used in place of micronized talc due to nozzle blockage and increased twinning of the generated beads.

TABLE 10

Controlled release polymer layer of Nafamostat controlled release beads coating solution (80:20 Eudragit RS:Eudragit RL)

| Component | % w/w | Quantity (g)[1] |
|---|---|---|
| Eudragit RS PO | 6.626 | 33.13 |
| Eudragit RL PO | 0.576 | 2.88 |
| Triethyl Citrate | 0.720 | 3.60 |
| Syloid 244FP | 1.800 | 9.00 |
| Acetone*,[2] | 34.396 | 171.98 |
| Isopropanol, Anhydrous*,[2] | 51.576 | 257.88 |
| Water for irrigation*,[2] | 4.306 | 21.53 |
| Total solution | 100.000 | 500.00 |

Figure 15:
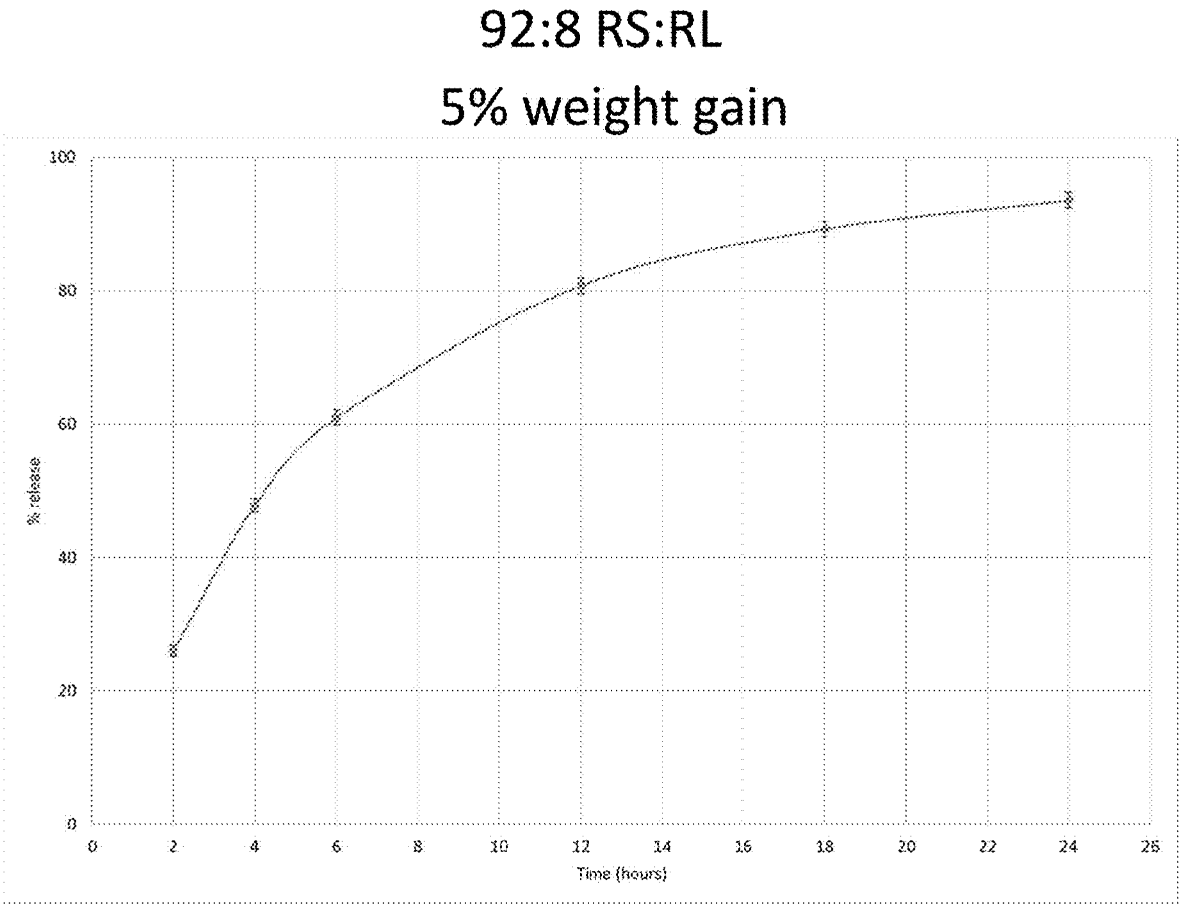
FIG. 15 shows a comparison of release profiles of nafamostat from the controlled release beads having a 92:8 (Eudragit RS: Eudragit RL) ratio at 5% weight gain.

*Removed during the process
[1]ER coating suspension 9.72% solids
[2]Acetone/Isopropanol/water = 38.10:57.13:4.77 ratio The Procept Fluid Bed was set up as previously described and 250 g of nafamostat active agent layer containing beads (as described above) were weighed out and loaded into the vessel. The process ran for approximately 3 hours, achieving a theoretical 15% weight gain. The bulk beads were cured in the vessel at 40° C. for 15 minutes and then transferred into a metal tray and placed into the oven overnight, at 40° C. LOD was taken following overnight curing and found to be comparable to previous batches (0.85%). By controlling the nozzle pressure and flow carefully, the filters didn't exceed 40 mbar allowing the process to continue running smoothly. Approximately 385 g coating solution was sprayed resulting in a coating weight gain of 15%. Using a 600 μm sieve, the ER coated beads were screened for twins. FIG. 15 shows a comparison of release profiles of nafamostat from the controlled release beads having a 92:8 (Eudragit RS: Eudragit RL) ratio at 5% weight gain.

Example 10: Preparation of Controlled Release Nafamostat Compositions

Nafamostat compositions containing controlled release beads were prepared. Each controlled release bead includes a microcrystalline cellulose core and an active agent layer of nafamostat mesylate and a controlled release polymeric coating layer. The active agent layer of nafamostat mesylate was prepared as set forth in Example 4. A polymeric controlled release coating solution with a 92:8 ratio of Eudragit RS: Eudragit RL was prepared as summarized in Table 11. Syloid 244FP was used in place of micronized talc due to nozzle blockage and increased twinning of the generated beads.

TABLE 11

Controlled release polymer layer of Nafamostat controlled release beads coating solution (80:20 Eudragit RS:Eudragit RL)

| Component | % w/w | Quantity (g)[1] |
|---|---|---|
| Eudragit RS PO | 5.306 | 26.53 |
| Eudragit RL PO | 1.768 | 8.84 |
| Triethyl Citrate | 0.708 | 3.54 |
| Syloid 244FP | 3.538 | 17.69 |
| Acetone*,[2] | 33.787 | 168.94 |
| Isopropanol, Anhydrous*,[2] | 50.663 | 253.32 |
| Water for irrigation*,[2] | 4.230 | 21.15 |
| Total solution | 100.000 | 500.00 |

Figure 16:
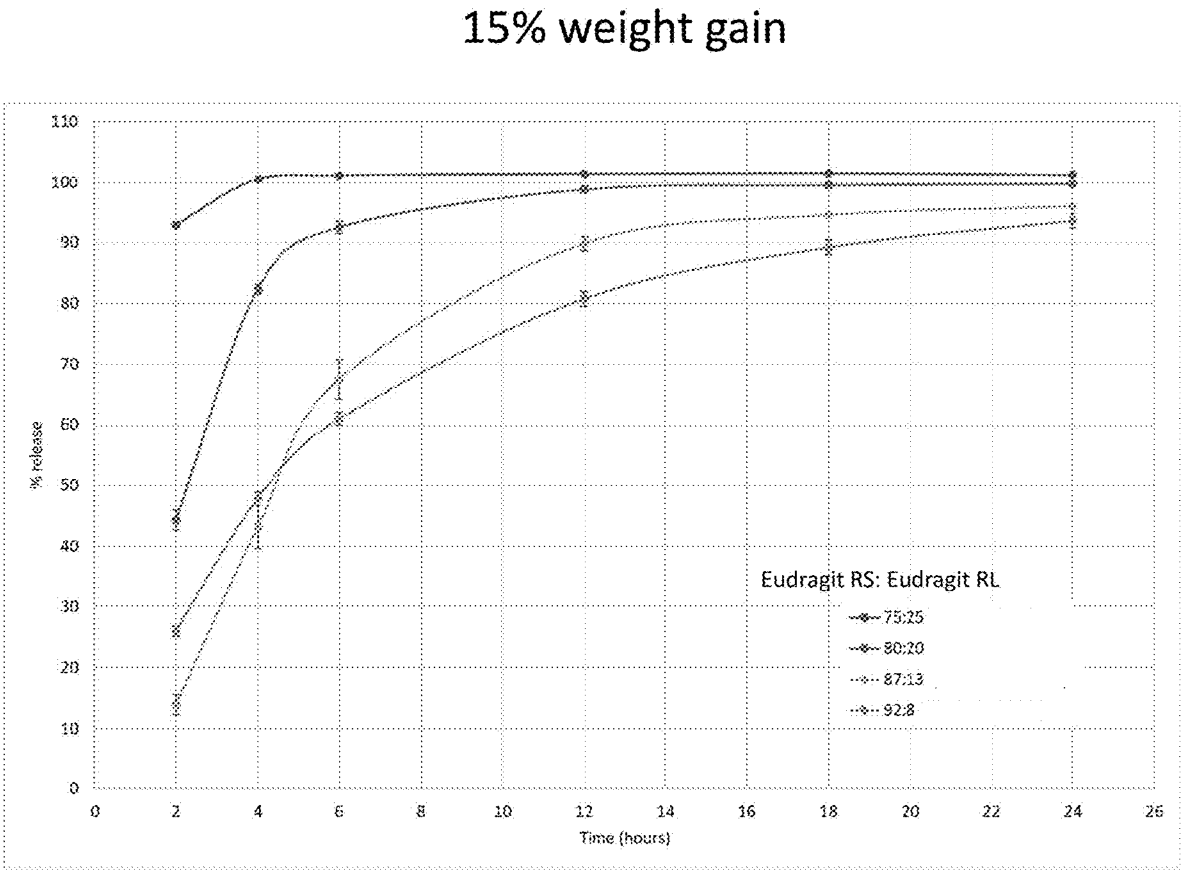
FIG. 16 shows a comparison of mean release profiles of nafamostat from the controlled release beads at 15% weight gain with different ratios of Eudragit RS: Eudragit RL in the controlled release polymeric layer having syloid 244FP in place of micronized talc.

*Removed during the process
[1]ER coating suspension 9.72% solids μ
[2]Acetone/Isopropanol/water = 38.10:57.13:4.77 ratio The Procept Fluid Bed was set up as previously described and 250 g of nafamostat active agent layer containing beads (as described above) were weighed out and loaded into the vessel. The process ran for approximately 3 hours, achieving a 14.7% weight gain. The bulk beads were cured in the vessel at 40° C. for 10 minutes and then transferred into a metal tray and placed into the oven overnight, at 40° C. LOD was taken following overnight curing and found to be comparable to previous batches (0.68%). By controlling the nozzle pressure and flow carefully, the filters didn't exceed 40 mbar allowing the process to continue running smoothly. Approximately 324 g coating solution was sprayed resulting in a theoretical coating weight gain of 14.7%. Using a 600 μm sieve, the ER coated beads were screened for twins. FIG. 16 shows a comparison of mean release profiles of nafamostat from the controlled release beads at 15% weight gain with different ratios of Eudragit RS: Eudragit RL in the controlled release polymeric layer having syloid 244FP in place of micronized talc.

Example 11: Extended Release and Immediate Release Nafamostat in Minipigs

Drug formulations containing nafamostat using extended release beads were synthesized. In other words, present Example 3 studied the effect of substituting nafamostat in the drug formulations of Examples 1 and 2 (herein referred to as immediate release) with nafamostat in an extended release bead. The effect of the nafamostat formulation was measured by blood concentrations of oxycodone, which is released from KC-8 that was also administered.

The extended release drug formulation was a capsule containing multiple beads, wherein each bead had a spherical core of microcrystalline cellulose that was coated with an active agent layer, which was then coated with a controlled release layer (i.e. extended release layer or modified release layer). The active agent layer included a mixture of nafamostat and hypomellose, which is also known as hydroxylpropyl methylcellulose (HPMC). The controlled release layer included various ratios of Polymer A and Polymer B, along with triethyl citrate and talc. Polymer A was poly (ethylacrylate, methyl-methacrylate and chlorotrimethylammonioethyl methacrylate) containing about 50 mEq of quaternary ammonium groups per 100 g of polymer. Polymer A was purchased as Eudragit RL. Polymer B poly (ethylacrylate, methyl-methacrylate and chlorotrimethylammonioethyl methacrylate) containing about 25 mEq of quaternary ammonium groups per 100 g of polymer. Polymer B was purchased as Eudragit RS.

As shown in the table below, five different types of controlled release beads were synthesized based on different ratios of Polymer A to Polymer B.

| Controlled Release Bead | Polymer A:Polymer B Ratio |
|---|---|
| Bead B | 50:50 |
| Bead C | 20:80 |
| Bead D | 80:20 |
| Bead E | 100:0 |
| Bead F | 87:13 |

Six different studies were conducted, as described in the table below. In each study KC-8 was administered along with nafamostat. Whereas Studies 1-5 contained either immediate release or extended release nafamostat, Study 6 included equal amounts of both immediate release and extended release nafamostat.

| Study Number | Immediate Release Nafamostat | Extended Release Nafamostat Beads | Notes |
|---|---|---|---|
| 1 | No | Bead B, C, or D | |
| 2 | No | Yes; Bead D; either 0, 10, 50, or 100 mg | FIG. 7 |
| 3 | No | Yes; Bead E; either 0, 1, 5, or 10 mg/kg | FIG. 8 |
| 4 | Yes; either 0, 50, or 100 mg | No | FIG. 9 |
| 5 | No | Yes; Bead F; either 0, 50, or 100 mg | FIG. 10 |
| 6 | Yes; either 0, 25, or 100 mg | Yes; Bead F; either 0, 25, or 100 mg | FIG. 11 |

Study 1 involved administering KC-8 and either Beads B, C, or D. It was found that Beads B and C corresponded to high maximum concentrations of oxycodone, whereas Beads D caused lower maximum concentrations of oxycodone.

Figure 7:
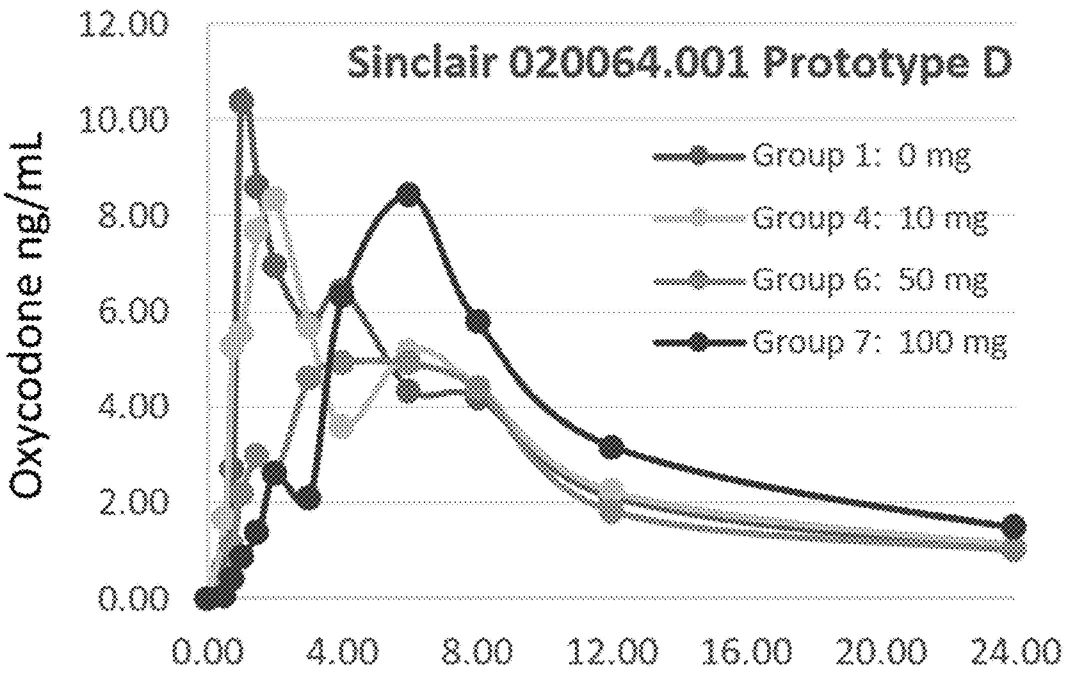
FIG. 7 shows the oxycodone concentration of minipigs administered KC-8 along with various amounts of nafamostat in Beads D.

Study 2 involved administered KC-8 to minipigs with either no nafamostat (control) or 10, 50, or 100 mg of nafamostat in Beads D. The results are shown in FIG. 7. It was found that increasing the nafamostat concentration from 0 to 10 and then 50 mg resulted in delaying Tmax from 2 to 4 hr and produced a decrease in the maximum oxycodone concentration from 10 ng/ml to about 5 ng/ml. It was found that 100 mg nafamostat Bead D resulted in delaying Tmax to 6 hr.

Figure 8:
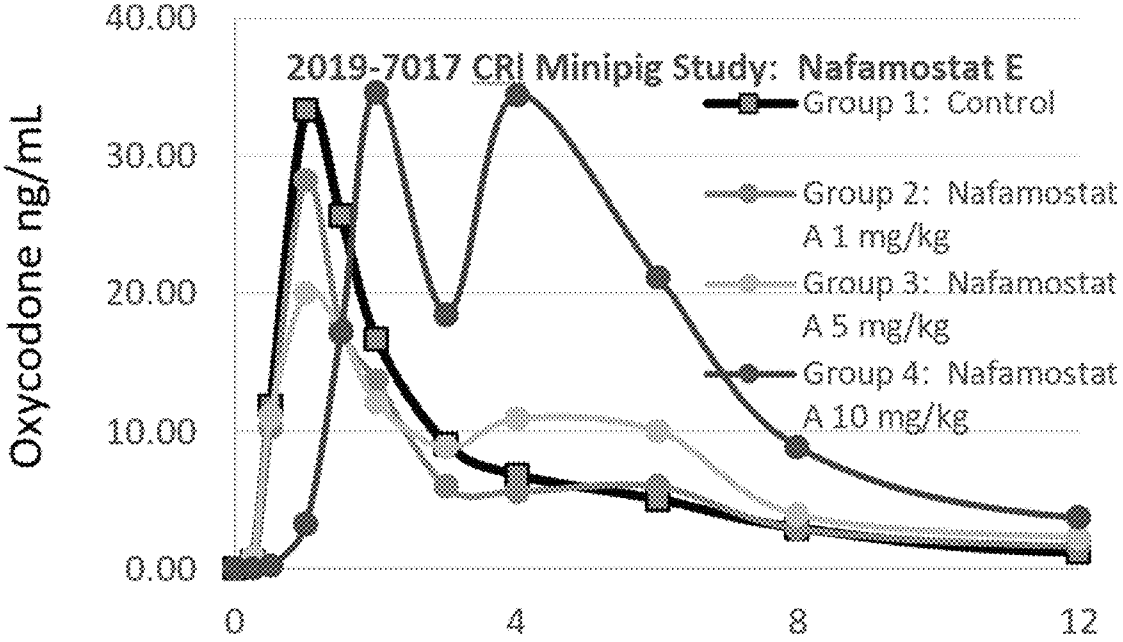
FIG. 8 shows oxycodone concentration in minipigs administered KC-8 along with nafamostat in Beads E.

Study 3 involved administering Beads E, which had a 100:0 ratio of Polymer A to Polymer B. When increasing the nafamostat concentration from 0 to 1 to 5 mg/kg the maximum oxycodone concentration decreased from about 34 ng/ml to about 20 ng/ml with a Tmax of 1 hr, as shown in FIG. 8. The 10 mg/kg nafamostat delayed the time to reach maximum oxycodone concentration (Tmax) to 2 hr.

Figure 9:
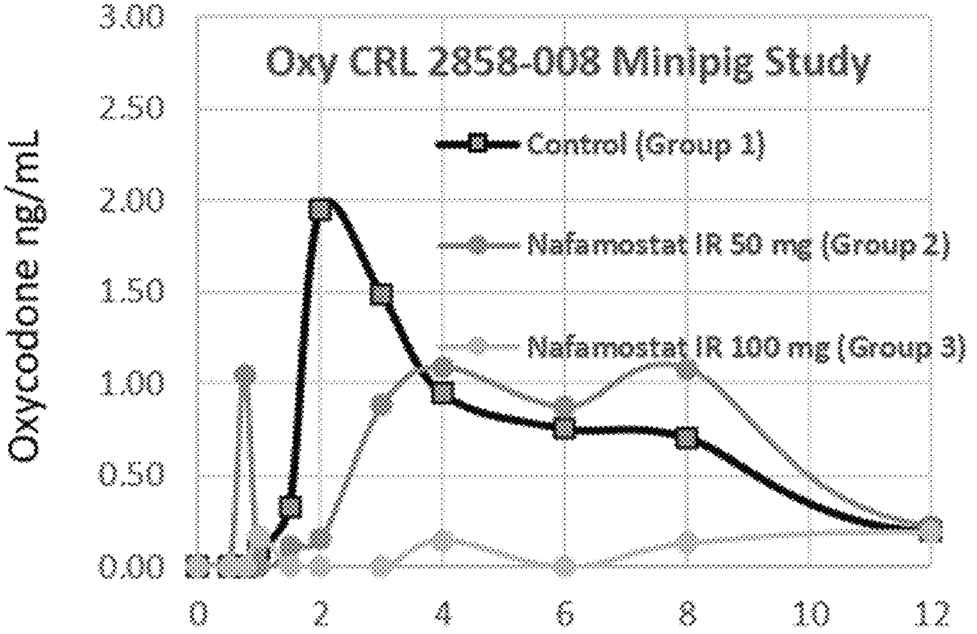
FIG. 9 shows oxycodone concentration in minipigs administered KC-8 with immediate release nafamostat.

Study 4 involved administering immediate release nafamostat that was not part of an extended release bead, as shown in FIG. 9. Increasing the amount of immediate release nafamostat from 0 to 50 mg resulted in a decrease of maximum oxycodone from 2 to 1 ng/ml. Further increasing immediate release nafamostat to 100 mg further decreased the maximum oxycodone to about 0.2 ng/ml.

Figure 10:
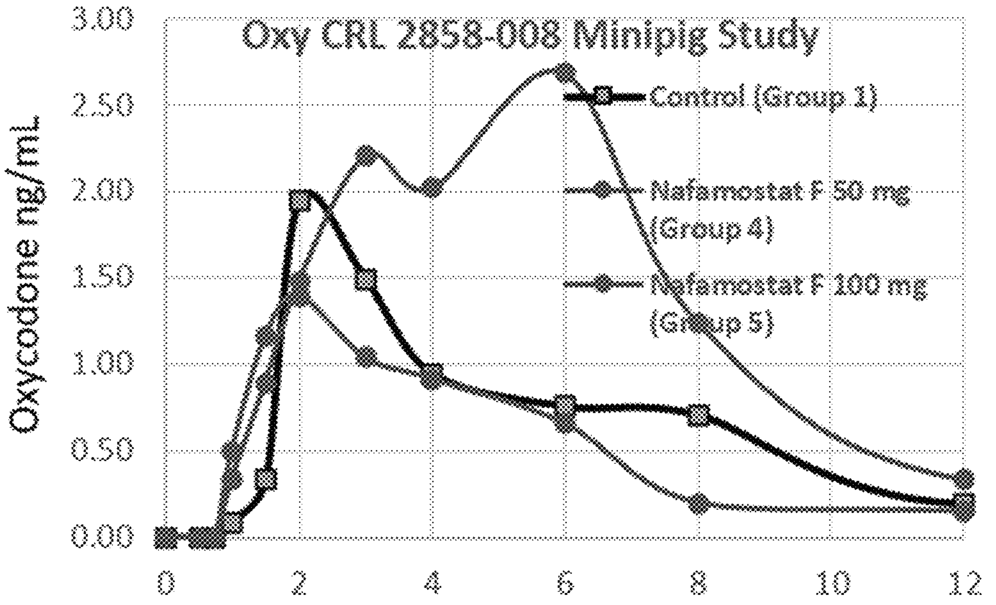
FIG. 10 shows oxycodone concentration in minipigs administered nafamostat in Beads F.

Study 5 involved administering nafamostat in Beads F. As shown in FIG. 10, the maximum oxycodone was 2 ng/ml with no nafamostat but only about 1.5 ng/ml with 100 mg of nafamostat in Beads F with a Tmax of 2 hr. Increasing the nafamostat dose to 100 mg resulted in a Tmax of oxycodone blood levels of 6 hr.

Figure 11:
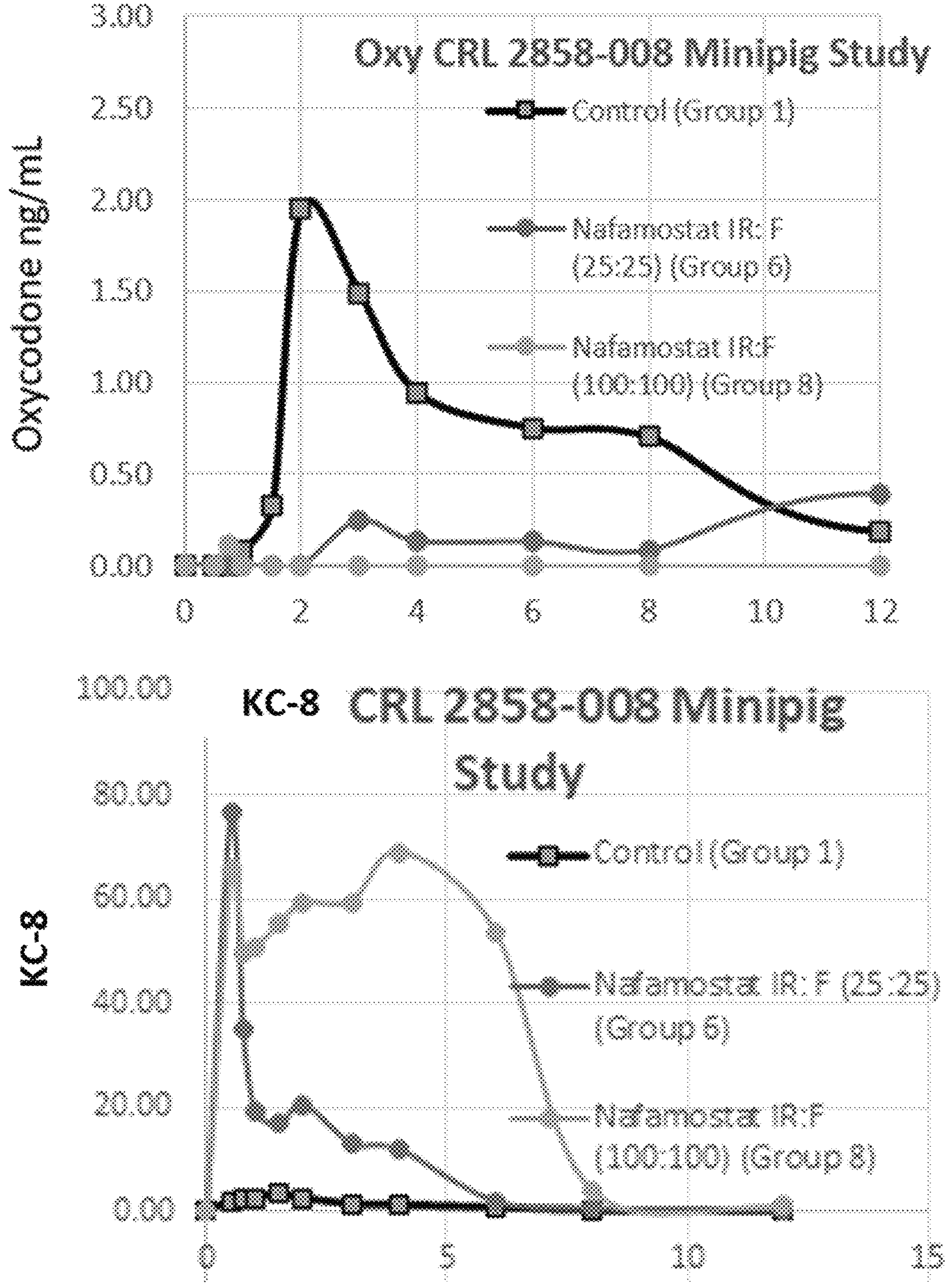
FIG. 11 shows oxycodone and KC-8 concentration in minipigs administered a combination of immediate release nafamostat and nafamostat in Beads F.

Study 6 involved administering an equal amount of both immediate release nafamostat and Beads F nafamostat. In particular, the minipigs received either no nafamostat (control), 25 mg of immediate release and 25 mg of Bead F nafamostat, or 100 mg of immediate release and 100 mg of Bead F nafamostat. FIG. 11 shows not only the concentration of oxycodone, but also the concentration of the oxycodone derivative of KC-8. Increasing the amount of Bead F nafamostat in combination with immediate release nafamostat decreased the maximum oxycodone concentration from about 2 ng/ml to about 0.3 or 0.1 ng/ml. Concurrently, KC-8 concentrations increased with increasing Bead F nafamostat in combination with immediate release nafamostat.

Example 12: Human Trials with KC-8 and Nafamostat in Immediate and Extended Release Formulations Human trials can be conducted wherein the effect of immediate and extended release nafamostat on KC-8 metabolism can be examined.

The study can involve modifying the dosage of nafamostat and/or the ratio of Polymer A to Polymer B in the extended release nafamostat beads, such as depending on the observations regarding oxycodone concentrations in the blood of the subjects. In other words, the controlled release layer containing Polymers A and B can be modified such that the release kinetics can be modified for optimal concentrations of oxycodone in subject blood. In some cases the formulation can also include nafamostat that is not within the controlled release beads, e.g. so that it can in some cases rapidly be available for pharmaceutical effect.

A Single Dose 2-Part Study to Evaluate the Pharmacokinetics of Oxycodone, KC-8, PFR06082, and Nafamostat, when KC-8 Solution is Co-Administered, as an Immediate Release Solution and/or Extended Release (ER) Capsule Formulations in Healthy Subjects.

The primary objective of Part 1 can be to assess the pharmacokinetics (PK) of oxycodone, when KC-8 solution is administered alone and with nafamostat as an immediate-release (IR) solution and/or extended-release (ER) capsule prototypes. The primary objective of Part 2 can be to determine the effect of the selected combinations of nafamostat IR solution and/or ER prototype capsule(s) on the PK of oxycodone at multiple dose levels of KC-8 solution and the selected nafamostat IR/ER formulation.

Part 1 Methodology

Part 1 of the study has a 6-period, randomized, open-label design. It is planned to enroll 24 healthy subjects, with roughly equal numbers of males and females who will take part in all 6 periods in Part 1. The 24 enrolled subjects will consist of an even number of males and an even number of females (eg, 12 males and 12 females; 14 males and 10 females etc), with a roughly equal number of males and females if possible. Subjects will then be randomized between 2 groups (Group 1 or Group 2) of 12 subjects each, to achieve approximately 8 evaluable subjects per group.

In both groups, subjects will receive the KC-8 solution alone (reference; Period 1) and concomitantly with nafamostat (as an IR solution and/or ER prototype capsule[s], in Periods 2 to 6). In addition, prior to and following each regimen in all periods, subjects will receive blocking doses of the opiate antagonist naltrexone to reduce the opioid-related side effects.

Both groups are planned to be dosed in parallel (with some flexibility in the dosing day for scheduling purposes); however, after Period 3 (Regimens 1C and 2C) there is the option for the groups to merge. Groups may be merged for subsequent periods (with all subjects receiving the same regimen for any dosing period) to gain increased precision of PK parameters in regimens likely to be progressed in future studies. If this option is progressed, there is also the option for the merged group to be split into Group 1 and Group 2 again for subsequent regimens based on emerging PK and safety data.

Interim reviews of the safety and PK data for oxycodone, KC-8 and PFR06082 to 48 h post-dose will take place after Periods 2, 3, 4 and 5 to decide upon the following:

- Nafamostat formulation(s) to dose (dose of IR solution, and/or release rate and dose of ER prototype capsule[s], as applicable) in the subsequent period;
- After Period 3 only: whether to merge or split the groups;
- After Period 4 only (for each group if Period 5 will be split): The prandial status (fed vs. fasted) for Period 5;
- After Period 5 only (for each group if Period 6 will be split): The dose levels for both the KC-8 solution and nafamostat formulations in Period 6.

Extended-release prototype capsule formulations will be selected from a 2-dimensional design space describing formulation variables for release rate (determined by the Eudragit RS: RL coating ratio 90% release in 2 to 16 h) and dose (1 to 100 mg).

Note that the nafamostat formulation (IR and/or ER) to be dosed in the fed state in Period 5 will be the formulation selected to be dosed in Part 2 of the study.

The regimens presented on the next page (the IMPs KC-8 and nafamostat, and the NIMP naltrexone) will be administered in a sequential manner to each group.

Part 2 Methodology

Part 2 of the study has a 5-period, non-randomized, open-label design. It is planned that the 12 healthy subjects will be enrolled into Part 2 of the study, to achieve a minimum of 8 evaluable subjects.

Subjects will receive the KC-8 solution concomitantly with the selected combination of nafamostat IR solution and/or ER prototype capsule(s) from Part 1 (defined as 1 dose unit; ie, 1 Dose Unit=KC-8 solution[25 mg]+ the selected nafamostat formulation[IR and/or ER prototype capsule {ZZ mg}]). In each period the subjects will receive an increased number of dose units. Hence a fixed ratio of KC-8: nafamostat will be administered at increasing dose levels, to simulate overdose. Note, this is a simulation of an overdose; however, the total dose of KC-8 will not exceed 200 mg (equivalent to 80 mg oxycodone) as was delivered in a Phase 1 single ascending dose study, and therefore will remain within safe and well tolerated levels. In addition, the fixed ratio selected for Part 2 will be a higher KC-8/nafamostat dose ratio than Part 1. It is expected that a 10:1 dose ratio of KC-8 vs nafamostat will be used in Part 2. It is planned that Part 1 will use a lower dose, ratio ranging from 1:1 to 2.5:1; however, these ratios may be modified based on emerging PK data from Part 1.

In addition, prior to and following each regimen, subjects will receive doses of the opiate antagonist naltrexone to reduce the opioid-related side effects.

The combination of nafamostat IR solution and/or ER prototype capsule(s) and dose to be administered in Period 1 (Regimen G) will be determined following interim review of the Part 1 safety and PK data out to 48 h post-dose. Interim reviews of the safety and PK data to 48 h post-dose will also take place after Periods 1, 2, 3 and 4 to decide if escalation to the next planned number of dose units may proceed, and the number of dose units to be administered. In addition, it is planned to assess nafamostat PK in Regimen K (Period 5), which is predicted to be the highest dose level administered. However, if this regimen doesn't administer the highest dose level in Part 2, there is an option to analyze previous regimens for nafamostat PK using the PK back-up samples from a previous regimen. This decision will take place during the interim review after Period 4.

There will be a final review after Period 5 in order to look at the interim data prior to data reporting in the Clinical Study Report.

The highest dose level of KC-8 solution to be administered in Part 2 will be 200 mg (8×25 mg), which is equivalent to 80 mg oxycodone. In previous SAD study with KC-8, doses of up to 200 mg (80 mg oxycodone) have been shown to be safe and well tolerated. The highest dose level of nafamostat that may be administered will be 200 mg, which has been shown to be safe and well tolerated from the 200 mg healthy volunteer SAD data.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112 (f) or 35 U.S.C. § 112 (6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or U.S.C. § 112 (6) is not invoked.

I claim:

1. A composition comprising nafamostat or a pharmaceutically acceptable salt thereof, wherein the composition provides for controlled release of the nafamostat or pharmaceutically acceptable salt thereof to a subject for an extended period of time, the composition comprising a plurality of controlled release beads, each bead comprising:

a core;

an active agent layer comprising nafamostat or a pharmaceutically acceptable salt thereof; and a controlled release layer comprising one or more polymers formulated in an amount sufficient to provide for controlled release of the nafamostat or pharmaceutically acceptable salt thereof.

2. The composition of claim 1, wherein the core comprises a cellulose polymer, or silicon dioxide, or a sugar selected from the group consisting of glucose, sucrose, lactose, mannitol, xylitol, and sorbitol.

3. The composition of claim 1, wherein the active agent layer further comprises a binder.

4. The composition of claim 1, wherein the controlled release layer comprises a combination of:

acrylate copolymer A comprising poly(ethylacrylate, methyl-methacrylate and chlorotrimethyl-ammonioethyl methacrylate) comprising about 50 mEq of quaternary ammonium groups per 100 g of polymer; and acrylate copolymer B comprising poly(ethylacrylate, methyl-methacrylate and chlorotrimethyl-ammonioethyl methacrylate) comprising about 25 mEq of quaternary ammonium groups per 100 g of polymer.

5. The composition of claim 4, wherein the controlled release layer comprises:

acrylate copolymer comprises: 95% by weight acrylate copolymer B and 5% by weight acrylate copolymer A; or acrylate copolymer comprises: 93% by weight acrylate copolymer B and 7% by weight acrylate copolymer A; or acrylate copolymer comprises: 92% by weight acrylate copolymer B and 8% by weight acrylate copolymer A; or acrylate copolymer comprises: 90% by weight acrylate copolymer B and 10% by weight acrylate copolymer A; or acrylate copolymer comprises 87% by weight acrylate copolymer B and 13% by weight acrylate copolymer A; or acrylate copolymer comprises: 80% by weight acrylate copolymer B and 20% by weight acrylate copolymer A; or acrylate copolymer comprises: 70% by weight acrylate copolymer B and 30% by weight acrylate copolymer A.

6. The composition of claim 1, wherein the controlled release layer comprises from 5% to 30% by weight of each of the plurality of beads.

7. The composition of claim 1, wherein one or more of the active agent layer and the controlled release layer further comprise a plasticizer.

8. The composition of claim 1, wherein each of the plurality of beads comprises from 5% to 20% by weight of the nafamostat or a pharmaceutically acceptable salt thereof.

9. The composition of claim 1, wherein the composition comprises a plurality of controlled release beads, each bead comprising:

a microcrystalline cellulose core;

an active agent layer comprising nafamostat or a pharmaceutically acceptable salt thereof and a water soluble methylcellulose polymer; and a controlled release layer comprising:

a first polymer comprising poly(ethylacrylate, methyl-methacrylate and chlorotrimethyl-ammonioethyl methacrylate) containing about 50 mEq of quaternary ammonium groups per 100 g of polymer;

a second polymer comprising poly(ethylacrylate, methyl-methacrylate and chlorotrimethyl-ammonioethyl methacrylate) containing about 25 mEq of quaternary ammonium groups per 100 g of polymer;

triethyl citrate; and a glidant selected from micronized talc and an amorphous silica, wherein the controlled release layer is formulated to provide for controlled release of the nafamostat or pharmaceutically acceptable salt thereof.

10. The composition of claim 9, wherein the controlled release layer is formulated to provide for release of 60% or more of the nafamostat or pharmaceutically acceptable salt thereof within 6 hours after administration.

11. The composition of claim 1, wherein the controlled release layer is formulated to provide for release of 90% or more of the nafamostat or pharmaceutically acceptable salt thereof within 6 hours of administration.

12. The composition of claim 1, further comprising nafamostat or a pharmaceutically acceptable salt thereof in an immediate release form that provides for an immediate release of nafamostat or pharmaceutically acceptable salt thereof to the subject.

13. A method comprising administering to the respiratory system of a subject in need thereof a composition of claim 1, wherein administering to the respiratory system of the subject comprises inhalation, intratracheal instillation, intratracheal delivery, insufflation, nebulization or a combination thereof.

14. The composition of claim 1, wherein the controlled release layer is formulated to provide for release of 90% or more of the nafamostat or pharmaceutically acceptable salt thereof within 4 hours of administration.

15. The composition of claim 1, wherein the controlled release layer is formulated to provide for release of 90% or more of the nafamostat or pharmaceutically acceptable salt thereof within 9 hours of administration.

* * * * *